US010286039B2

(12) United States Patent
Wu

(10) Patent No.: US 10,286,039 B2
(45) Date of Patent: May 14, 2019

(54) COMPOSITIONS AND METHODS FOR TREATING NEUTROPENIA

(71) Applicant: Children's Hospital Los Angeles, Los Angeles, CA (US)

(72) Inventor: Lingtao Wu, Rancho Palos Verdes, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 0 days.

(21) Appl. No.: 15/119,339

(22) PCT Filed: Feb. 18, 2015

(86) PCT No.: PCT/US2015/016447
§ 371 (c)(1),
(2) Date: Aug. 16, 2016

(87) PCT Pub. No.: WO2015/126989
PCT Pub. Date: Aug. 27, 2015

(65) Prior Publication Data
US 2017/0007672 A1  Jan. 12, 2017

Related U.S. Application Data

(60) Provisional application No. 61/941,233, filed on Feb. 18, 2014.

(51) Int. Cl.
| *A61K 38/19* | (2006.01) |
| *A61K 31/192* | (2006.01) |
| *A61K 31/196* | (2006.01) |
| *A61K 35/15* | (2015.01) |
| *A61K 35/12* | (2015.01) |
| *A61K 45/06* | (2006.01) |
| *C12N 5/0787* | (2010.01) |
| *A61K 31/69* | (2006.01) |
| *G01N 33/84* | (2006.01) |

(52) U.S. Cl.
CPC .......... *A61K 38/193* (2013.01); *A61K 31/192* (2013.01); *A61K 31/196* (2013.01); *A61K 31/69* (2013.01); *A61K 35/15* (2013.01); *A61K 45/06* (2013.01); *C12N 5/0642* (2013.01); *G01N 33/84* (2013.01); *A61K 2035/124* (2013.01); *C12N 2501/22* (2013.01); *G01N 2800/52* (2013.01)

(58) Field of Classification Search
None
See application file for complete search history.

(56) References Cited

U.S. PATENT DOCUMENTS

| 5,700,650 A | 12/1997 | Mak et al. |
| 2005/0003453 A1 | 1/2005 | Sarkar et al. |
| 2009/0176862 A1 | 7/2009 | Chandraratna et al. |
| 2011/0052574 A1 | 3/2011 | Dick et al. |
| 2012/0201884 A1 | 8/2012 | Gokaraju et al. |
| 2013/0165637 A1* | 6/2013 | Yan ..................... A61K 38/193 530/362 |
| 2014/0037600 A1 | 2/2014 | Yu et al. |
| 2015/0164836 A1 | 6/2015 | Wu |

FOREIGN PATENT DOCUMENTS

| AU | 2013270674 A1 | 12/2014 |
| AU | 2015219038 A1 | 8/2016 |
| BR | 11-2016-018938-8 A2 | 8/2017 |
| CA | 2874850 A1 | 12/2013 |
| CA | 2937340 A1 | 8/2015 |
| CN | 1816345 A | 8/2006 |
| CN | 104519879 A | 4/2015 |
| CN | 106413701 A | 2/2017 |
| CN | 201380041537.6 | 10/2018 |
| EA | 201101035 A1 | 2/2012 |
| EP | 1632241 A1 | 3/2006 |
| EP | 1633241 A1 | 3/2006 |
| EP | 2143428 A1 | 1/2010 |
| EP | 2858638 A1 | 4/2015 |
| EP | 3017533 A1 | 12/2016 |
| EP | 2858636 B1 | 9/2018 |
| HK | 1208630 A1 | 3/2016 |
| JP | 2001-506998 A | 5/2001 |
| JP | 2015523346 A | 8/2015 |
| JP | 2017508737 A | 3/2017 |

(Continued)

OTHER PUBLICATIONS

Dunn et al., Lenograstim, Drugs, 59, 681-717, 2000.*
Ding et al., Retinoid agonist Am80-enhanced neutrophil bactericidal activity arising from granulopoiesis in vitro and in a neutropenic mouse model, Blood, 121, 996-1007, 2013.*
Beekman et al. G-CSF and its receptor in myeloid malignancy. Blood, 115, 5131-5136, 2010. (Year: 2010).*
Jia Bei et al., Immunomodulatory Effect of Neutrophils in Bacterial Infection, World Notes on Antibiotics, 2004, vol. 25 (2), pp. 61-63 cited in CN 201380041537.6 Office Action dated May 18, 2017, 24 pages.
PCT/US2015/016447 International Preliminary Report on Patentability dated Sep. 1, 2016; 11 pages.

(Continued)

*Primary Examiner* — Elly-Gerald Stoica
(74) *Attorney, Agent, or Firm* — Nixon Peabody LLP; Linda B. Huber; Suwei Zhu

(57) ABSTRACT

The invention relates methods of using a retinoid agonist and a G-CSF or an analog thereof to treat, prevent, reduce the likelihood of having, reduce the severity of and/or slow the progression of a condition in a subject. The retinoid agonist and the G-CSF or the analog thereof may be provided in a single composition or in separate compositions. A therapeutically effective amount of the retinoid agonist and the G-CSF or the analog thereof may be administered to the subject concurrently or sequentially. Conditions treatable with the methods and compositions include but are not limited to various forms of neutropenia and microbial infections. The invention also relates to methods for determining the efficacy of the treatments described herein.

17 Claims, 27 Drawing Sheets

(56) References Cited

FOREIGN PATENT DOCUMENTS

| | | | |
|---|---|---|---|
| JP | 6295249 B2 | 2/2018 | |
| KR | 20150035983 A | 4/2015 | |
| KR | 20160113302 A | 9/2016 | |
| MX | 2014014930 A | 7/2015 | |
| NZ | 702415 A | 4/2016 | |
| RU | 2191009 C2 | 10/2002 | |
| RU | 2007124325 | 1/2009 | |
| RU | 2008142899 A | 5/2010 | |
| RU | 2014153988 A | 7/2016 | |
| WO | 2004100972 A1 | 11/2004 | |
| WO | 2006010503 A2 | 2/2006 | |
| WO | 2006020891 A2 | 2/2006 | |
| WO | 2006071451 A1 | 7/2006 | |
| WO | 2010/028388 A1 | 3/2010 | |
| WO | 2013169864 A2 | 11/2013 | |
| WO | 2013185105 A1 | 12/2013 | |
| WO | WO2013185105 | * 12/2013 | ........... A61K 31/165 |
| WO | 2015126989 A1 | 8/2015 | |

OTHER PUBLICATIONS

PCT/US2013/044828 International Search Report and Written Opinion dated Nov. 8, 2013; 6 pages.

PCT/US2013/044828 International Preliminary Report on Patentability dated Dec. 9, 2014; 5 pages.

PCT/US2015/016447 International Search Report and Written Opinion dated May 14, 2015; 11 pages.

EP Application No. 13800873.5 Partial Supplementary Search Report dated Dec. 4, 2015; 8 pages.

EP Application No. 13800873.5 Extended Search Report dated May 2, 2016; 14 pages.

Kagechika et al. Retinobenzoic Acids. Structure-Activity Relationships of Aromatic Amides with Retinoidal Activity.

Schon et al. A comparative study of three methods to evaluate an intervention to improve empirical antibiotic therapy for acute bacterial infections in hospitalized patients. Scandinavian Journal of Infectious Diseases (2011). 43:251-257.

Sekiguchi et al. Clinical Observations with Clarithromycin in Pediatrics. Japanese Journal of Antibiotics (1989). 42(2):411-419. Abstract Only.

Tohda et al. The effects of retinoic acid analogues on the blast cells of acute myeloblastic leukemia in culture. International Journal of Oncology (1994). 4:1311-1314.

Uruno et al. All-trans retinoic acid and a novel synthetic retinoid tamibarotene (Am80) differentially regulate CD38 expression in human leukemia HL-60 cells: possible involvement of protein kinase C-δ. Journal of Leukocyte Biology (2011). 90:235-247.

Visser et al. Neutropenia, neutrophil dysfunction, and inflammatory bowel disease in glycogen storage disease type Ib: Results of the European Study on Glycogen Storage Disease Type 1. The Journal of Pediatrics (2000). 137:187-191.

Shibakura et al. A Retinoic Acid Receptor-a (RARa) Selective Agonist Modulates Procoagulant Activity of Acute Promyelocytic Cells and Induces Their Differentiation into Neutrophils. Blood (1998). 91(2)124-728.

Tobita et al. Treatment with a New Synthetic Retinoid, Am80, of Acute Promyelocytic Leukemia Relapsed from complete Remission Induced by All-trans Retinoic Acid. Blood (1997). 90(3):967-973.

Tsurumi et al., The Combined Effects of All-Trans Retinoic Acid and Granulocyte Colony-Stimulating Factor as a Differentiation Induction Therapy for Acute Promyelocytic Leukemia, Internal Medicine, 1993, vol. 32(8), pp. 648-650.

Wanjing Ding, Study on the Effect and Mechanism of Retinoid Agonist AM80-Enhanced Neutrophil Bactericidal Activity Arising from Granulopoiesis, 2013, CDFD, Medical and Health Science and Technology, No. 11, pp. E079-30. Published between Oct. 16, 2013 and Nov. 15, 2013.

EP 15751576.8 Extended Search Report dated Sep. 18, 2017, 11 pages.

Hematol, Acute Promyelocytic Leukemia and Differentiaion Therapy: Molecular Mechanisms of Differentiation, Retinoic Acid Resistance and Novel Treatments, APL and Differentiation Therapy, 2009, vol. 26, pp. 47-61.

Hubel et al., Current Status of Granulocyte (Neutrophil) Transfusion Therapy for Infectious Diseases, The Journal of Infectious Disease, 2001, vol. 183, pp. 321-328.

Naina et al., Successful Treatment of Relapsed and Refactory Extramedullary Acute Promyelocytic Leukemia with Tamibarotene, Journal of Clinical Oncology, 2011, vol. 29(18), pp. e534-e536.

Tsurumi et al., The Combined Effects of All-Trans Retinoic Acid and Granulocyte Colony-Stimulating Factor as a Differentiation Induction Therapy for Acute Promyelocytic Leukemia, Internal Medicine, 1993, vol. 32(8), pp. 548-650.

Usuki et al., Administration of Granulocyte Colony-Stimulating Factor during Remission Induction Therapy with All-Trans Retinoic Acid for Acute Promyelocytic Leukemia, Internal Journal of Hematology, 1996, vol. 64, pp. 213-219.

Gianni, AM580, A Stable Benzoic Derivative of Retinoic Acid, Has Powerful and Selective Cyto-Differentiating Effects on Acute Promyelocytic Leukemia Cells, 1996, Blood, vol. 87(4), pp. 1520-1531.

Masue Imaizumi, Molecular Mechanism of the Leukemogenesis and Differentiation-Induction in Acute Promyelocytic Leukemia, 2002, The Japanese Journal of Pediatric Hematology, vol. 16, pp. 50-61.

Montrone et al., Retinoids as Critical Modulators of Immune Functions: New Therapeutic Perspectives for Old Compounds, 2009, Endocrine, Metabolic & Immune Disorders, vol. 9(2), pp. 1-19.

Zhong, Novel Retinoic Acid Receptor Alpha Agonists for Treatment of Kidney Disease, 2011, PLoS One, vol. 6(11), e27945.

Huston et al., Agents under Investigation for the Treatment and Prevention of Neutropenia, 2007, Expert Opinion on Investigational Drugs, vol. 16(11), pp. 1831-1840.

* cited by examiner

D

BM neutrophil recovery (day 5)
Second layer

| Group | Total(#) $1\times10^4$ | Neutrophil(#) $1\times10^4$ | Neutrophil (%) |
|---|---|---|---|
| Blank | 12.3 | 4.2 | 34.0 |
| Vehicle | 42.0 | 6.9 | 16.4 |
| GCSF | 128.9 | 70.9 | 55.0 |
| Am80 | 83.6 | 22.6 | 27.0 |
| A+G | 187.8 | 72.6 | 38.6 |

Third layer

| Group | Total(#) $1\times10^4$ | Neutrophil(#) $1\times10^4$ | Neutrophil (%) |
|---|---|---|---|
| Blank | 89.7 | 56.9 | 63.4 |
| Vehicle | 39.2 | 7.8 | 19.8 |
| GCSF | 92.8 | 45.3 | 48.8 |
| Am80 | 49.0 | 9.9 | 20.3 |
| A+G | 45.9 | 26.4 | 57.7 |

Morphology Differentiation
Second layer

Blank  Vehicle  G25  A0.5  A0.5+G25

Third layer

Blank  Vehicle  G25  A0.5  A0.5+G25

E    PB neutrophil recovery (day 5)

Mononuclear layer

| Group | Total(#) $1\times10^4$ | Neutrophil(#) $1\times10^4$ | Neutrophil (%) |
|---|---|---|---|
| Blank | 11.4 | 3.6 | 32.1 |
| Vehicle | 22.8 | 11.4 | 49.9 |
| GCSF | 20.1 | 13.8 | 68.9 |
| Am80 | 12.8 | 6.1 | 47.7 |
| A+G | 43.4 | 29.0 | 66.9 |

Neutrophil layer

| Group | Total(#) $1\times10^4$ | Neutrophil(#) $1\times10^4$ | Neutrophil (%) |
|---|---|---|---|
| Blank | 82.4 | 61.5 | 74.6 |
| Vehicle | 10.5 | 2.9 | 27.3 |
| GCSF | 44.8 | 32.9 | 73.4 |
| Am80 | 45.0 | 14.9 | 33.2 |
| A+G | 45.0 | 31.7 | 70.5 |

Morphologic differentiation

Mononuclear layer

Blank    Vehicle    G25    A0.5    A0.5+G25

Neutrophil layer

Blank    Vehicle    G25    A0.5    A0.5+G25

COMPOSITIONS AND METHODS FOR TREATING NEUTROPENIA

CROSS-REFERENCE TO RELATED APPLICATIONS

This application is a National Phase of International Application No. PCT/US2015/016447 filed Feb. 18, 2015, currently pending, which designated the U.S. and that International Application was published under PCT Article 21(2) in English, which also includes a claim of priority under 35 U.S.C. § 119(e) to U.S. provisional patent application No. 61/941,233 filed Feb. 18, 2014, the entirety of which is hereby incorporated by reference.

STATEMENT REGARDING FEDERALLY-SPONSORED RESEARCH

This invention was made with government support under Grant No. CA120512 awarded by the National Institutes of Health. The government has certain rights in the invention.

FIELD OF THE INVENTION

The invention relates to compositions, methods and kits for treating a condition with retinoid agonists and granulocyte colony-stimulating factor (G-CSF or GCSF). The invention also relates to compositions, methods and kits for treating a condition with ex vivo modified cells (such as granulocytes [for example, neutrophils, eosinophils and basophils] derived from hematopoietic stem cells [HSCs]) for cell therapies. The condition includes but is not limited to various forms of neutropenia.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Neutrophils, the most common granulocytes, constitute up to 70% of circulating leukocytes that primarily defend against pathogen infections. Cancer chemotherapy-induced neutropenia is a hematological disorder marked with a significant decrease in the number of neutrophils in the bloodstream, leading to susceptibility to microbial infections. About 15-40% of cancer patients require treatment delay and/or dose reduction because of chemotherapy-induced neutropenia. Mortality rate due to neutropenia is about 5% in patients with solid tumors and 11% in some hematological malignancies.

Neutrophil production requires balanced proliferation and differentiation during granulopoiesis of hematopoietic stem cells (HSC). GCSF has been used to treat acquired and congenital neutropenia for more than two decades as it promotes granulopoiesis of HSC to regenerate neutrophils. However, the large numbers of neutrophils regenerated in response to GCSF administration are immature, thus resulting in an ineffective GCSF therapy that fails to reduce both infection and infection-related mortality of cancer chemotherapy-induced neutropenia (CCIN) patients. Evidence supports that the cost-effectiveness of primary prophylactic use of GCSF for CCIN is inconclusive, and recent studies have shown that primary prophylactic use of GCSF during the first course of chemotherapy was associated with a 57% increase in overall healthcare costs. In the US, the cost of CCIN ranged from $1,893 per outpatient episode to $38,583 per febrile neutropenia hospitalization. Substantial differences in the clinical and economic burden of CCIN exist depending on cancer types, co-morbidities and types of infections. Owing to the decreased inflammatory response in CCIN, the symptoms and signs of infection are attenuated or even absent. Hence, chemotherapy comprises the majority of costs for both febrile neutropenia (33.5%) and non-febrile neutropenia (40.6%) patients. The estimated cost for febrile neutropenia hospitalization (FNH) only for 2015 is about $2.1 billion. This cost does not include the cost for treatment of non-febrile neutropenia, relapsed cancer patients requiring new chemotherapy, congenital neutropenia, idiopathic severe chronic neutropenia, cyclic neutropenia, and radiation-induced neutropenia. Hence, despite preventive use of GCSF, neutropenia still remains a devastating issue for cancer patients, with substantial morbidity, mortality, and healthcare cost. As such, alternative modes of treatment are urgently needed for these neutropenic patients.

Herein, the inventor demonstrates synergistic effect of a combination of a retinoid agonist (e.g., Am80) and G-CSF on reducing infection and infection-related mortality. For treating neutropenia and neutropenia-related conditions, provided herein are compositions, methods and kits that capitalize on the synergistic effect of retinoid agonist (e.g., Am80) with G-CSF on regeneration of mature neutrophils against infection and infection-related mortality.

SUMMARY OF THE INVENTION

Various embodiments of the present invention provide a method of treating, preventing, reducing the severity of and/or slowing the progression of a condition in a subject. The method may comprise or may consist of: providing a retinoid agonist; providing a G-CSF or an analog thereof; and administering a therapeutically effective amount of the retinoid agonist and the G-CSF or the analog thereof to the subject, thereby treating, preventing, reducing the severity of and/or slowing the progression of the condition in the subject. In various embodiments, the retinoid agonist and the G-CSF or the analog thereof may be in one composition or separate compositions. In various embodiments, the method may further comprise providing and administering a chemotherapeutic and/or an antimicrobial agent to the subject.

Various embodiments of the present invention provide a composition comprising a retinoid agonist and a G-CSF or an analog thereof. In various embodiments, the composition may further comprise a chemotherapeutic and/or an antimicrobial agent.

Various embodiments of the present invention provide a kit for treating, preventing, reducing the severity of and/or slowing the progression of a condition in a subject. The kit comprises: a quantity of retinoid agonist; a quantity of G-CSF or an analog thereof; and instructions for using the retinoid agonist and the G-CSF or the analog thereof to treat, prevent, reduce the severity of and/or slow the progression of the condition in the subject. In various embodiments, the kit may further comprise a chemotherapeutic and/or an antimicrobial agent and instructions of using the chemotherapeutic and/or the antimicrobial agent to treat, prevent, reduce the severity of and/or slow the progression of the condition in the subject.

Various embodiments of the present invention provide a method of generating mature granulocytes. The method includes providing a cell (e.g., a HSC, a bone marrow granulocytic progenitor cell and a hematopoietic CD34+ cell) and stimulating the cell with a retinoid agonist and a G-CSF or an analog thereof, thereby generating mature granulocytes. Various embodiments of the present invention further provide a composition comprising regenerated mature granulocytes. In various embodiments, the composition further comprises a retinoid agonist and a G-CSF or an analog thereof. In certain embodiments, the granulocytes are neutrophils.

Various embodiments of the present invention provide a method of treating, preventing, reducing the severity of and/or slowing the progression of a condition in a subject. The method includes providing a cell (e.g., a HSC, a bone marrow granulocytic progenitor cell, and a hematopoietic CD34+ cell), stimulating the cell with a retinoid agonist and a G-CSF or an analog thereof, thereby generating granulocytes and administering the generated granulocytes to the subject, thereby treating the condition in the subject. In certain embodiments, the granulocytes are neutrophils. In various embodiments, generating granulocytes is stimulating formation of granulocytes.

Various embodiments of the present invention provide a method of treating, preventing, reducing the severity of and/or slowing the progression of a condition in a subject. The method includes providing a cell (e.g., a HSC, a bone marrow granulocytic progenitor cell, and a hematopoietic CD34+ cell), stimulating the cell with a retinoid agonist and a G-CSF or an analog thereof and administering the stimulated cell to the subject, thereby treating the condition in the subject.

Examples of the retinoid agonist include but are not limited to tamibarotene (Am80, retinobenzoic acid, Amnoid, Tamibaro), CH55, ITYA (ITYA-01115), Am580, BD4, or NRX195183 (also referred to as AGN195183), or their functional equivalents, analogs, or derivatives. Examples of the G-CSF or the analog thereof include but are not limited to a wild type G-CSF, a recombinant G-CSF, a G-CSF monomer or dimer, a recombinant human G-CSF (rhG-CSF) dimer, a G-CSF mutant, a G-CSF fusion protein, a G-CSF fragment, a modified G-CSF polypeptide, a PEGylated G-CSF, a glycosylated G-CSF, and a G-CSF modified with Y-shaped branched polyethylene glycol (YPEG-G-CSF) at a specific lysine (Lys 17).

Various compositions, methods and kits of the present invention find utility in the treatment of various conditions, including but not limited to various forms of neutropenia and neutropenia-related conditions. As non-limiting examples, the compositions, methods and kits of the present invention may be used in conjunction with cancer therapies (e.g., chemotherapy and radiation therapy) and/or treatments of microbial infections.

Various embodiments of the present invention provide methods for determining the efficacy of treatment in a subject in need thereof. The methods include providing a sample from a subject, wherein the subject has been administered an effective a retinoid agonist and an effective amount of G-CSF, assaying the levels production of reactive oxygen species (ROS) and determining that the treatment is efficacious if the ROS production is higher than that of a reference sample or determining that the treatment is not efficacious if the ROS production is same as the reference sample or lower relative to the reference sample.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
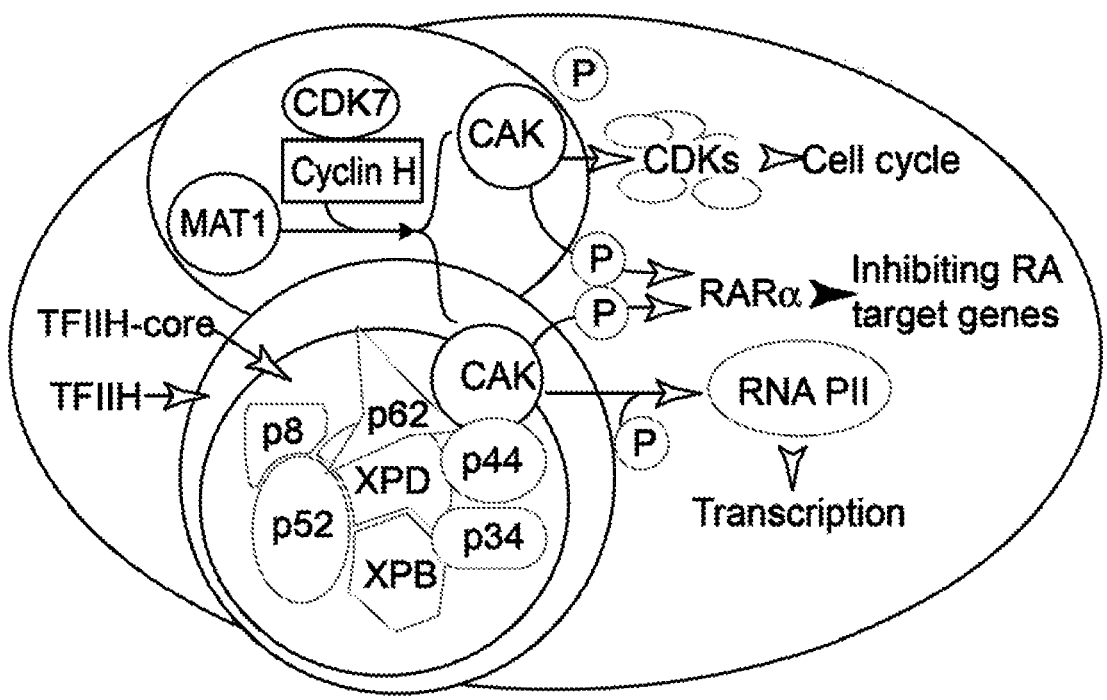
FIG. 1 depicts, in accordance with various embodiments of the invention, phosphorylation regulation of cell cycle, RA target gene expression, and general transcription by both free CAK and TFIIH-containing CAK.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of neutropenia, delay or slowing of neutropenia, and amelioration or palliation of symptoms associated with neutropenia.

As used herein, the term "administering," refers to the placement an agent as disclosed herein into a subject by a method or route which results in at least partial localization of the agents at a desired site.

"Conditions" and "disease conditions," as used herein may include, but are in no way limited to any form of neutropenia or neutropenia-related condition, disease or disorder. "Neutropenia" as used herein refers to a granulocyte disorder characterized by abnormally low levels of neutrophils in the blood. Neutropenia may be due to decreased production of white blood cells (for example, due to, including but not limited to therapeutic agents that affect the bone marrow, hereditary/congenital disorders that affect the bone marrow, alcoholism, hypersplenism, hyperthyroidism, Lupus, aplastic anemia, cancer (particularly blood cancers), radiation therapy, Vitamin B12, folate or copper deficiency and/or exposure to pesticides). Neutropenia may also be due to destruction of white blood cells (for example, due to, including but not limited to viral infection, acute bacterial infections, certain autoimmune diseases, chemotherapy treatments and/or therapeutic agents). Neutropenia may also be due to marginalization, sequestration and/or migration of white blood cells (for example, due to, including but not limited to, hemodialysis, malaria and/or bacterial infections). Certain medications such as flecainide, phenytoin, indomethacin, propylthiouracil, carbimazole, chlorpromazine, trimethoprim/sulfamethoxazole (cotrimoxazole), clozapine, ticlodipine and certain anti-psychotic medications may also result in neutropenia. The methods and compositions of the invention may be used to treat, inhibit, reduce the severity of and/or promote prophylaxis of neutropenia resulting from any of the above causes. The methods and compositions of the invention may also be used to treat, inhibit, reduce the severity of and/or promote prophylaxis of neutropenia-related conditions such as bacterial, fungal, viral, parasitic infections as well as radiation damage of innate immunity that result from any of the above causes of neutropenia by treating, inhibiting, reducing the severity of and/or promoting prophylaxis of neutropenia.

The term "sample" or "biological sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

Figure 4:
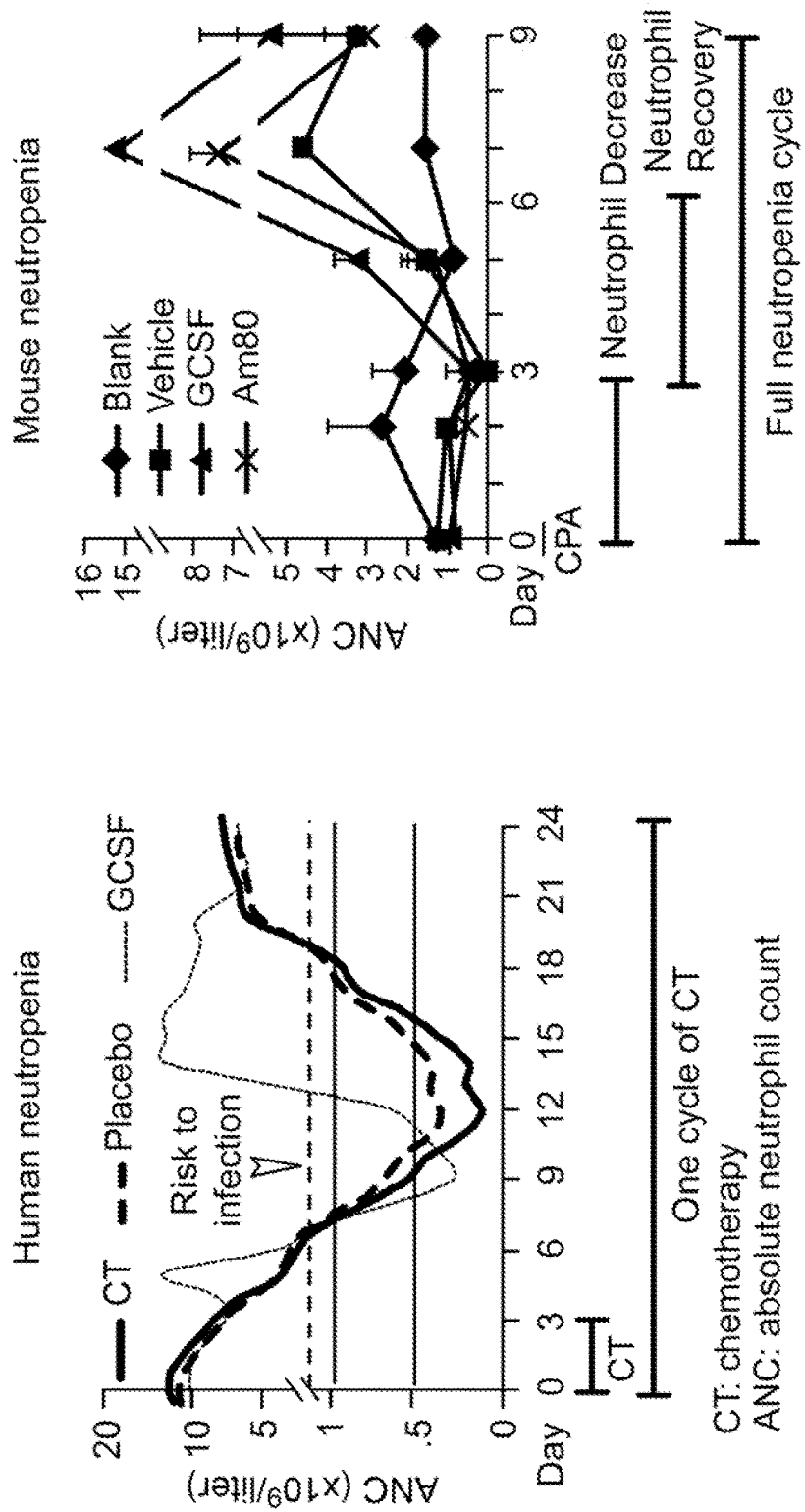
FIG. 4 depicts, in accordance with various embodiments of the invention, a comparison of chemotherapy induced neutropenia in Human (left panel) and Mouse (right) to establish that the mouse model resembles human neutropenia.

"Neutropenia-induction" or "neutrophil decrease" stage as used herein refers to cancer chemotherapy-induced neutropenia and coincides with a decrease in peripheral blood (PB) absolute neutrophil count (ANC) as shown in FIG. 4, left panel human days 0-12 and right panel mouse days 0-3.

"Neutropenia-recovery" or "Neutrophil-recovery" or "neutrophil induction" stage as used herein refers to a recovery in PB neutrophil numbers (ANC) following the nadir or trough. See FIG. 4 days 12-24 (left panel) and days 3-9 (right panel).

A "subject" can be one who has been previously diagnosed with or identified as suffering from or having a condition (e.g., neutropenia or neutropenia-related disorders) in need of treatment or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Granulocyte colony-stimulating factor (G-CSF or GCSF) induces a quick increase in the number of neutrophils in the bloodstream. Unfortunately, the neutrophils induced by G-CSF are poorly differentiated together with their impaired bactericidal functions, resulting from inadequate development of neutrophil effector functions during granulopoiesis early in the differentiation process.

Retinoic acid (RA) enhances self-renewal of hematopoietic stem cells (HSC) through retinoic acid receptor gamma (RARγ) activation while promoting differentiation of committed myeloid progenitors through RARα activation. Am-80 is an all-trans retinoic acid (ATRA or RA) agonist designed to selectively binding RARα but not RARγ. This selective property of Am80 can sufficiently promote granulocytic differentiation.

We recently discovered that Am-80 (tamibarotene) enhances modest myelopoietic expansion while inducing mature neutrophils superior to G-CSF in combating bacterial infection. This effect arises from Am80-induced selective activation of transcription factor RARα to induce novel selective expression of RA target genes via inhibiting RARα phosphorylation, which is mediated by the CAK complex regulating both cell cycle and general transcription.

Through a comprehensive in vivo study using various neutropenic mouse models, we have discovered that although Am-80 has significantly higher bactericidal activity than either G-CSF or Am80-G-CSF combination at neutrophil-decrease stage in neutropenic mouse model, it displays lower efficiency against bacterial infection at neutrophil-recovery stage than those induced by Am80-G-CSF combination. This indicates that: a) Am-80 may more effectively promote neutrophil differentiation than regenerating neutrophils from hematopoietic stem cells (HSC); b) Am80-induced significantly higher neutrophil bactericidal activity at the earlier developmental stage of mouse neutropenia (neutrophil-decrease stage) results from Am80-promoted differentiation of existing PB and BM granulocytic precursors into mature neutrophils; c) with low doses of Am80-GCSF treatment, Am80 can effectively differentiate GCSF-regenerated large numbers of granulocytic precursors into mature neutrophils against microbial infection; and d) Am80-GCSF combination is superior to GCSF in regeneration of mature neutrophils capable of reducing infection and infection-related mortality of neutropenic mice. The large number of neutrophils regenerated in response to G-CSF administration are immature, thus resulting in an ineffective bactericidal activity against infection at both neutrophil-decrease and neutrophil-recovery stages. By synergizing the effect of Am80 on enhancing neutrophil maturation together with the function of G-CSF in promoting myeloid expansion of HSC, we demonstrated that in the context of continual bacterial infection, combination of Am80 and G-CSF markedly reduces mortality of neutropenic mice than does either Am80 or GCSF alone.

We show that a combined Am80-GCSF treatment is significantly greater than Am80 at markedly reducing mortality of neutropenic mice in the presence of consistent bacterial infection, suggesting that although the selective activation of RARα by Am80 can contribute to effective neutrophil differentiation, Am80-mediated modest myeloid expansion does not meet the demand for a greater regeneration of neutrophils in the context of neutropenic condition undergoing consistent bacterial infection. These findings indicate a need of synergized effect of Am80 on enhancing neutrophil maturation together with the function of G-CSF in promoting myeloid expansion of HSC, which can overcome the ineffectiveness resulting from current G-CSF therapy for treatment of cancer chemotherapy-induced neutropenia.

Therefore, based on these findings, we propose to utilize a combination of retinoid agonist and G-CSF as an effective therapy to treat cancer chemotherapy-induced neutropenia and beyond, including but not limited to treatment of congenital neutropenia (e.g., Kostmann syndrome, cyclic neutropenia, and Chediak Higashi). We also propose using a combination of retinoid agonist and G-CSF for ex vivo granulocyte generation, particularly, neutrophils, for transfusion therapy to reduce the duration of neutropenia, and HSC transplantation of AML patients and as a radioprotective therapy against acute radiation syndrome.

Treatment Methods

Figure 6:
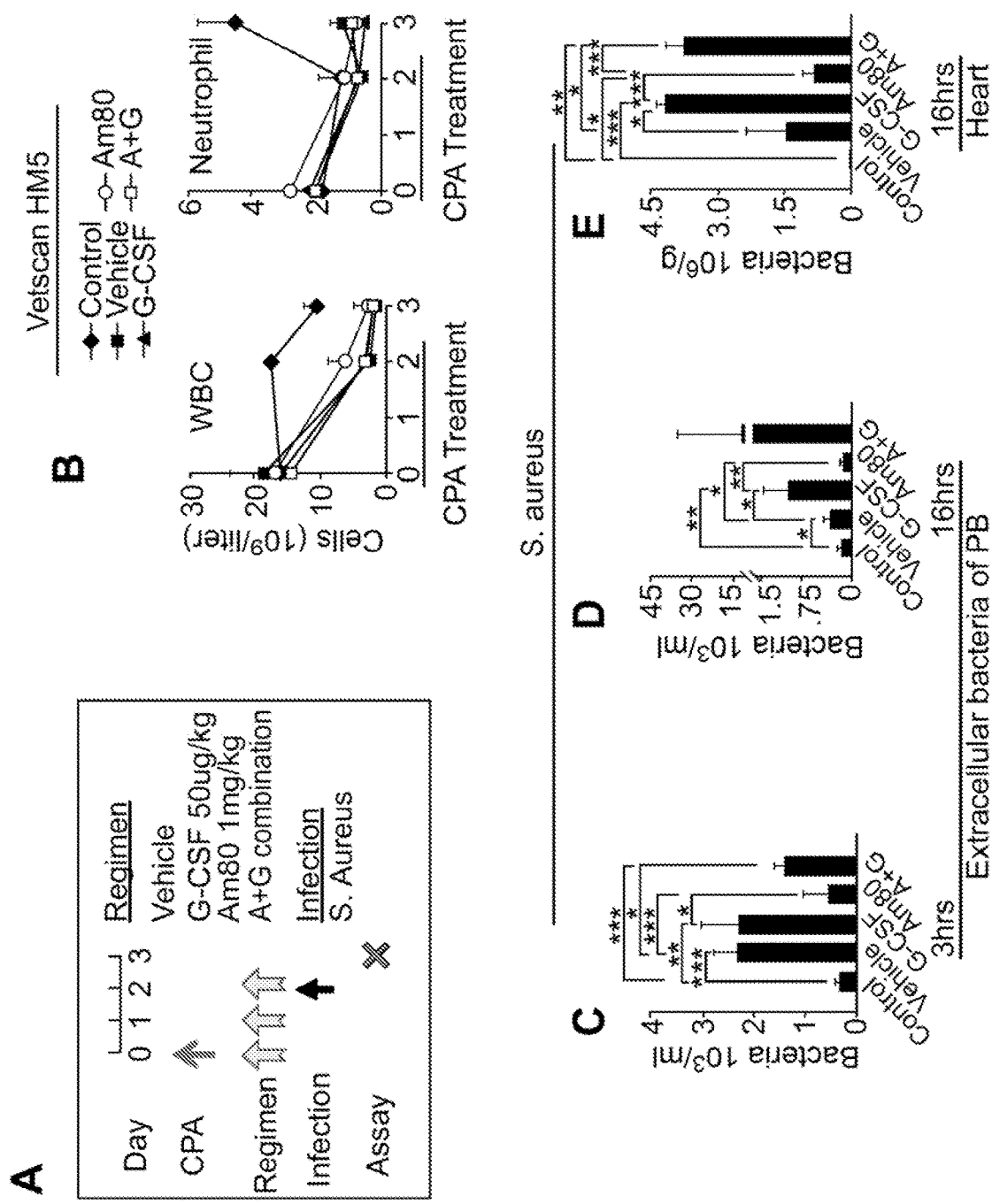
FIG. 6 depicts, in accordance with various embodiments of the invention, that neutrophils induced by medium dose of Am80 in neutropenic mice at neutrophil-decrease stage display greater bactericidal activity than those induced by G-CSF or Am80-GCSF.
Figure 7:
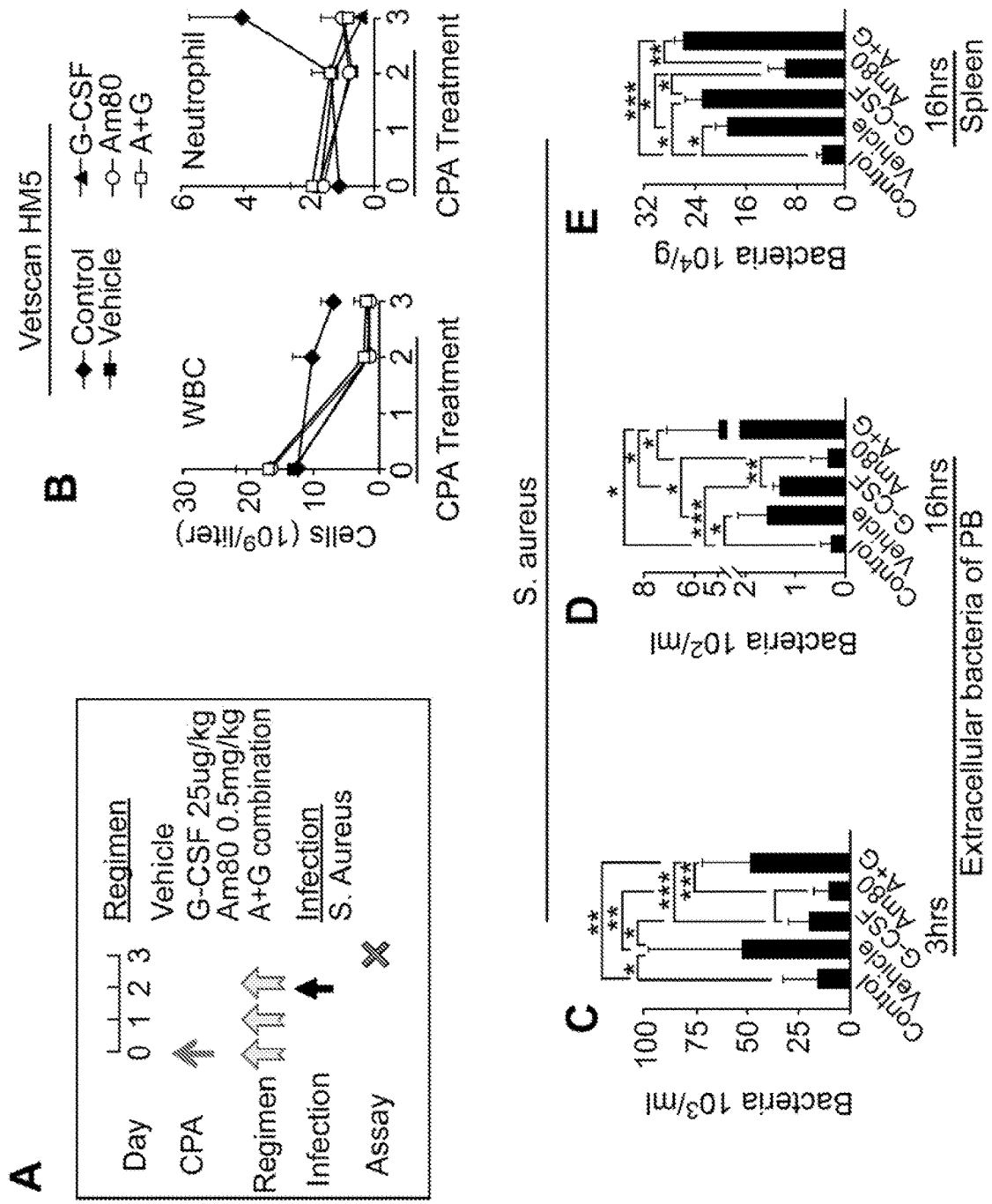
FIG. 7 depicts, in accordance with various embodiments of the invention, neutrophils induced by low dose of Am80 in neutropenic mice at neutrophil-decrease stage display greater bactericidal activity than those induced by GCSF or Am80-GCSF.
Figure 8:
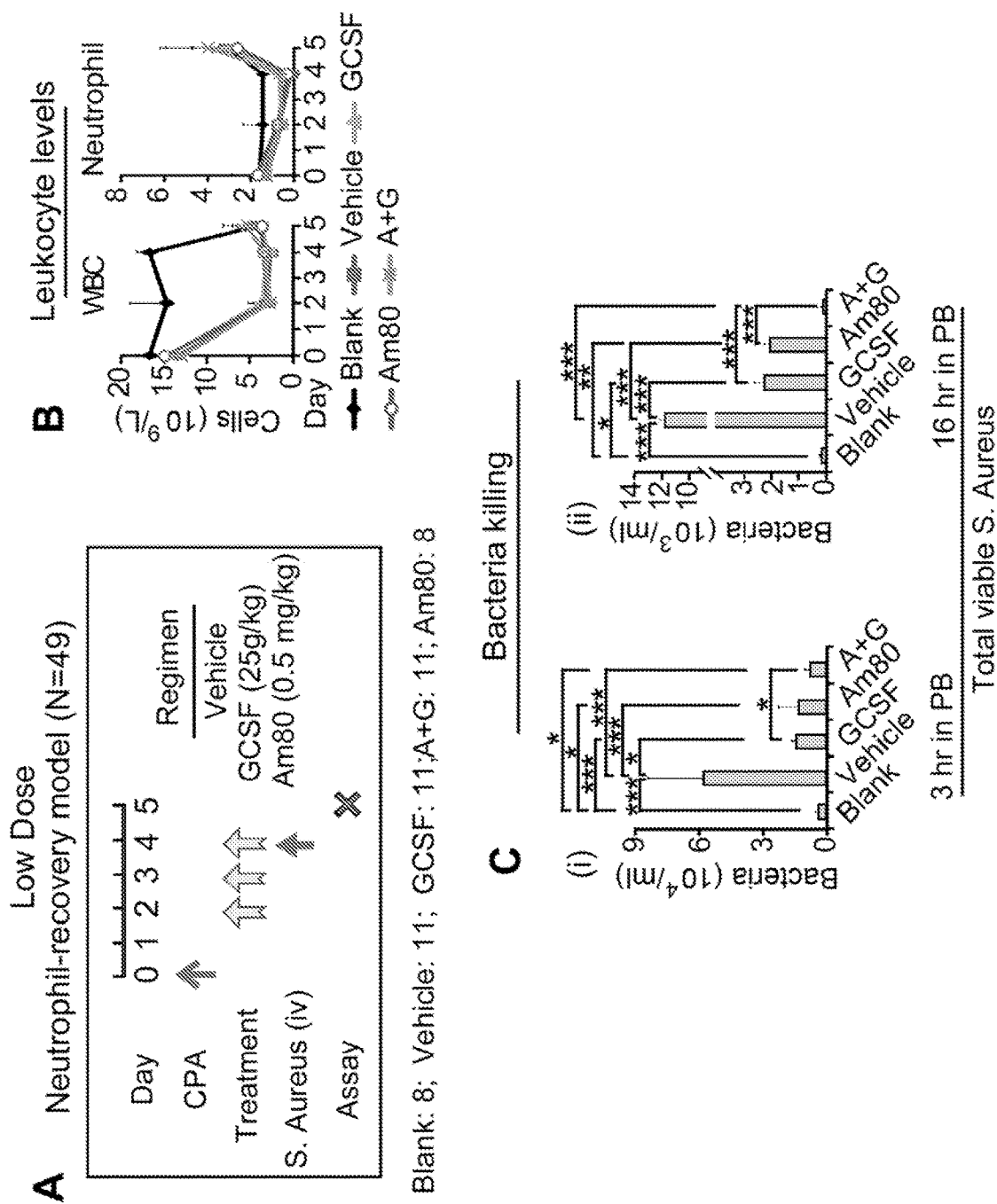
FIG. 8 depicts, in accordance with various embodiments of the invention, neutrophils induced by lower dose of Am80-GCSF combination in neutropenic mice at neutrophil-recovery stage display greater bactericidal activity than those induced by Am80 or GCSF.
Figure 8:
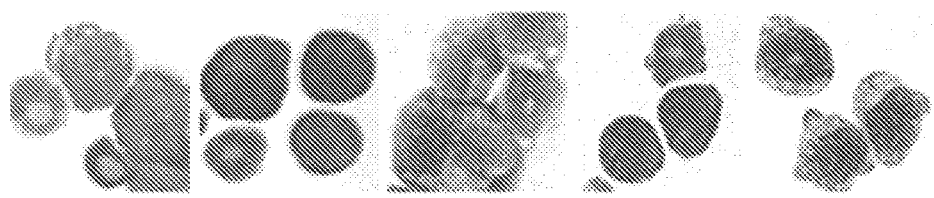
Figure 8:
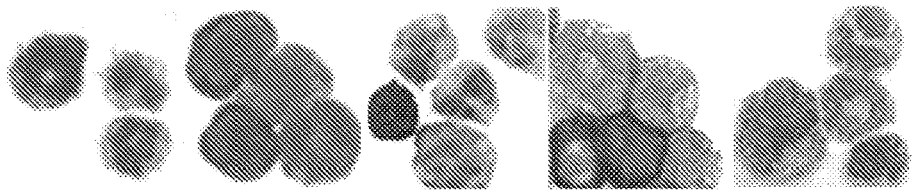
Figure 8:
Figure 8:
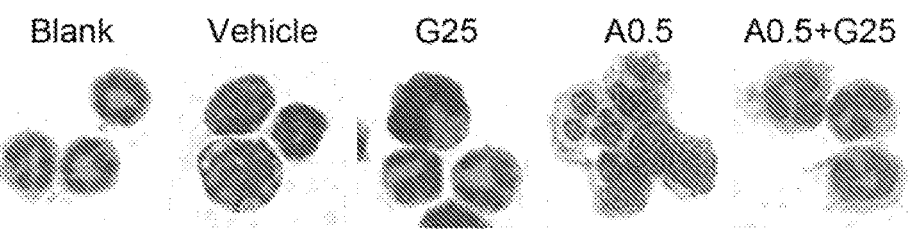
Figure 9:
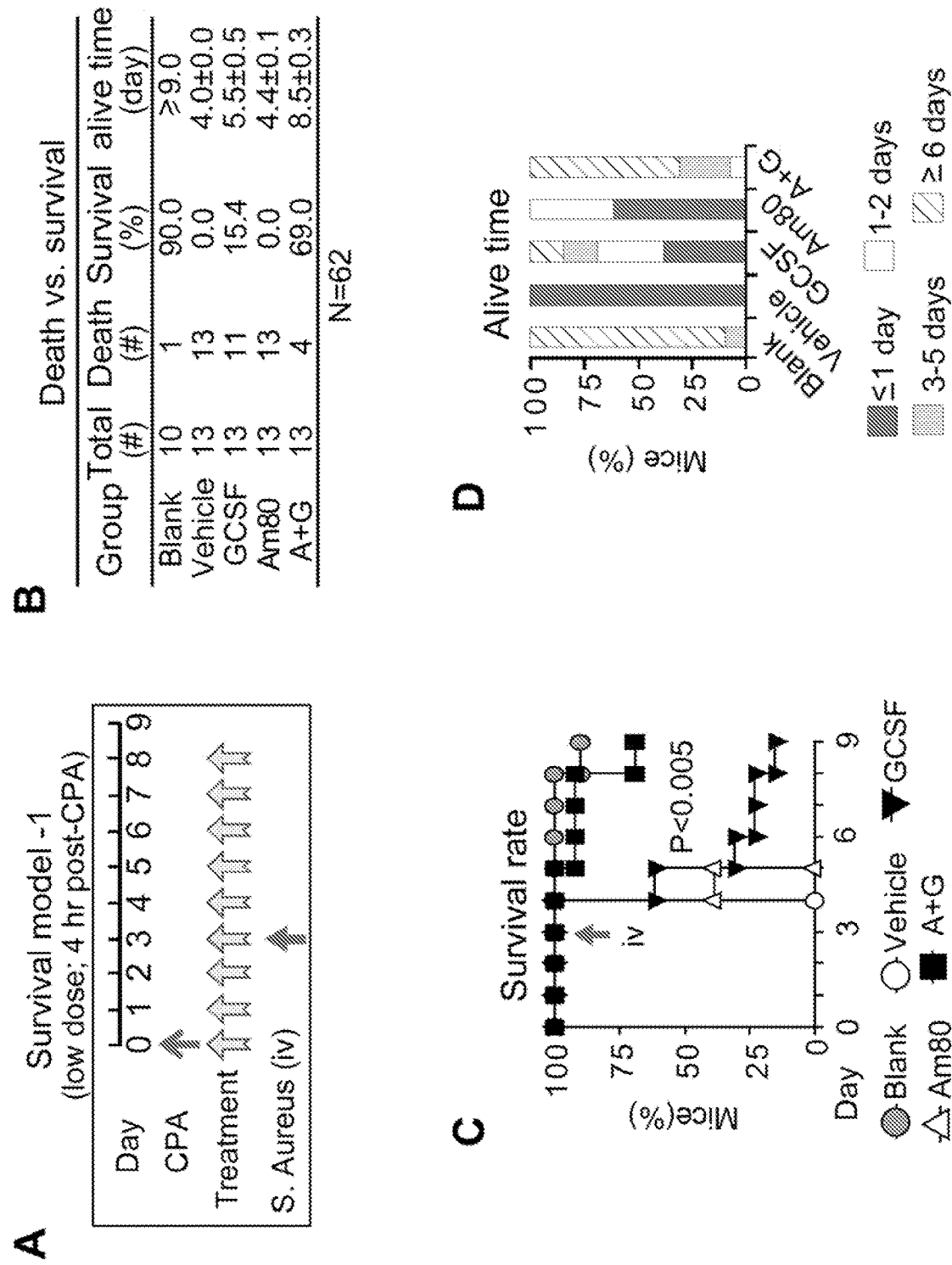
FIG. 9 depicts, in accordance with an embodiment of the invention, that survival mouse models demonstrate that low doses of Am80-GCSF reduce infection-related mortality of neutropenic mice.
Figure 9:
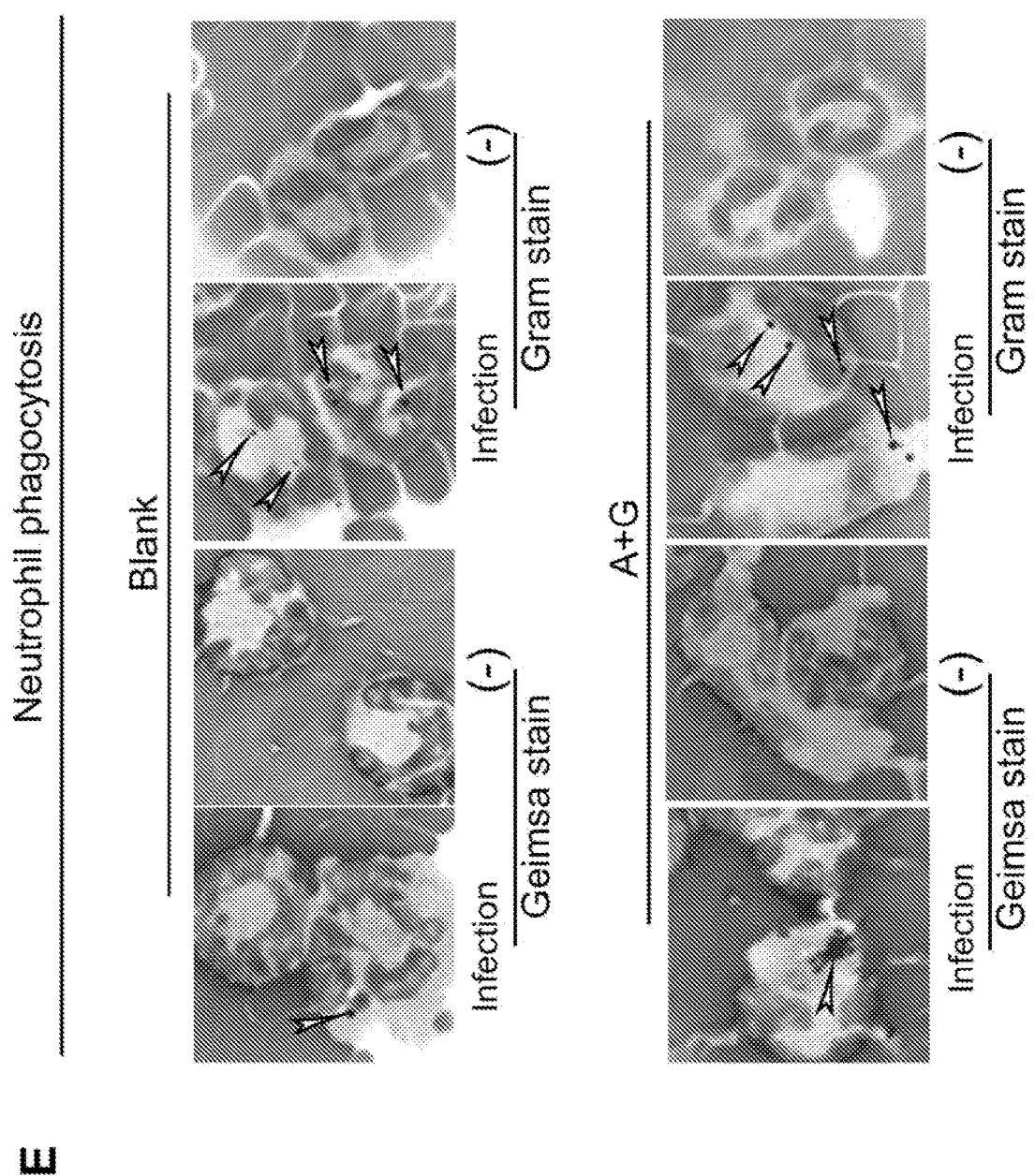
Figure 9:
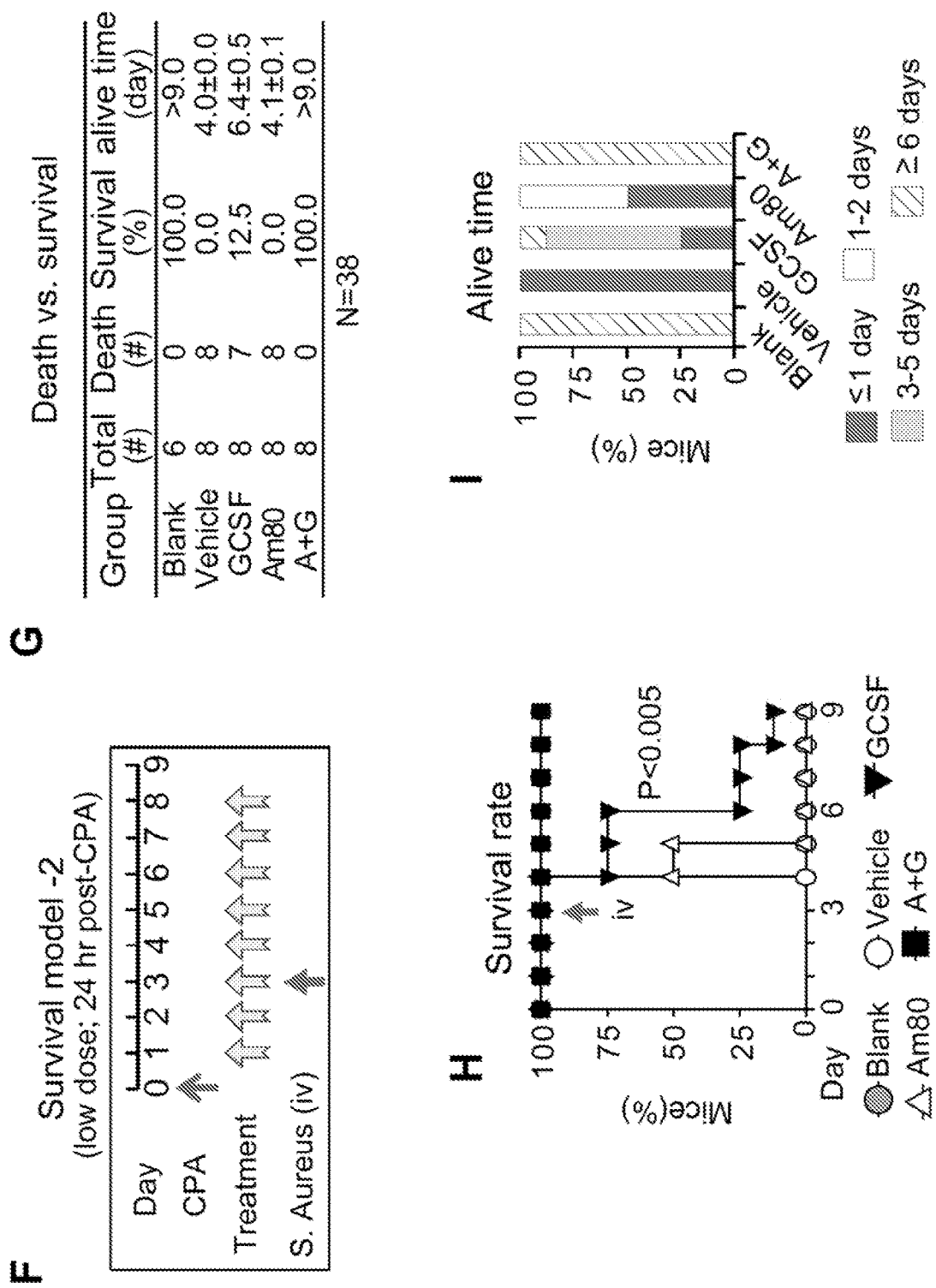
Figure 9:
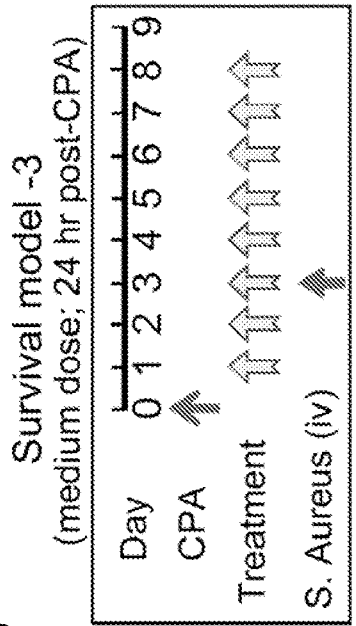
Figure 9:
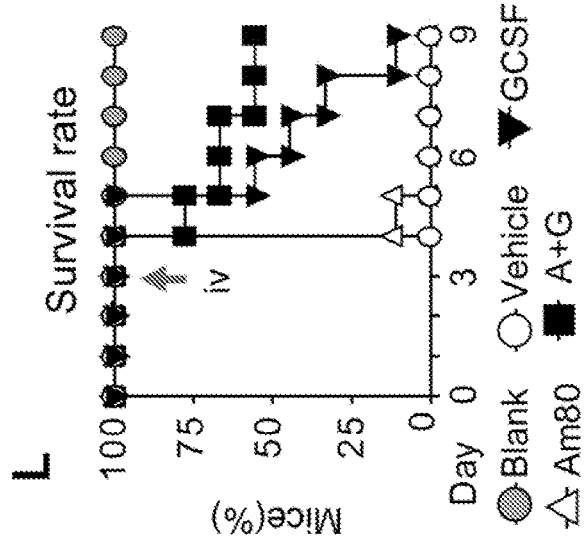

In established human and mouse neutropenic models (FIG. 4), either GCSF or Am80 cannot prevent neutrophil-decrease induced by chemotherapeutic drugs in early development of neutropenia. On the other hand, although quickly increased numbers of neutrophils by GCSF can shorten neutropenia duration during neutrophil-recovery period, these increased neutrophils are immature in fighting microbial infection. By using a series of neutropenic mouse models covering different stages of neutropenia, the inventor has addressed the question of whether Am80 alone or the combination of Am80-GCSF can effectively fight microbial infection. The results from neutrophil-decrease mouse models (FIGS. 6, 7) showed that, at early mouse neutropenia development stage when neutrophil regeneration from HSC is still inhibited by chemotherapeutic drugs, Am80 alone is superior to GCSF or Am80-GCSF in differentiating existing granulocytic precursors into mature neutrophils against infection. However, in the following neutrophil recovery period when granulopoiesis is progressively revived for regeneration of neutrophils, it is the Am80-GCSF combination, but not Am80 or GCSF alone, that synergistically regenerates and differentiates a large amount of mature neutrophils so as to fight bacterial infection (FIG. 8). Further, through the use of different neutropenic mouse survival models under the status of continual bacteremia, we show that Am80-GCSF synergy is sufficient to regenerate a sufficient amount of mature neutrophils to reduce infection and infection-related mortality of neutropenic mice (FIG. 9). These findings define that Am80 is more effective in promoting neutrophil differentiation than in regenerating neutrophils from HSC, and that by synergizing the Am80 effect of enhancing neutrophil differentiation together with GCSF function in promoting myeloid expansion of HSC, Am80-GCSF combination meets the demand for a greater amount of mature neutrophils to fight microorganisms in the neutropenic condition. Hence, our studies indicate that Am80-GSCF combination can coordinate myeloid expansion with neutrophil differentiation, providing an opportunity to develop effective cancer chemotherapy induced neutropenia (CCIN) therapy by use of Am80-GCSF combination treatment.

In various embodiments, the present invention provides a method of treating, preventing, reducing the likelihood of developing, reducing the severity of, promoting prophylaxis of and/or slowing the progression of a condition in a subject. The method may comprise or may consist of: providing a retinoid agonist; providing a G-CSF or an analog thereof; and administering a therapeutically effective amount of the retinoid agonist and the G-CSF or the analog thereof to the subject, thereby treating, preventing, reducing the likelihood of developing, reducing the severity of, promoting prophylaxis of and/or slowing the progression of the condition in the subject. In various embodiments, the retinoid agonist and the G-CSF or the analog thereof are in one composition. In other embodiments, the retinoid agonist and the G-CSF or the analog thereof are in separate compositions.

In accordance with various embodiments of the invention, the condition is neutropenia or microbial infection. In certain embodiments, the microbial infection is bacterial, viral, fungal or parasitic infection. In certain embodiments, the neutropenia is chemotherapy-induced neutropenia, congenital neutropenia, idiopathic neutropenia, cyclic neutropenia, autoimmune neutropenia; or radiation neutropenia.

In various embodiments, the present invention provides a method of treating, preventing, reducing the likelihood of developing, reducing the severity of, promoting prophylaxis of and/or slowing the progression of neutropenia in a subject. The method may comprise or may consist of: providing a retinoid agonist; providing a G-CSF or an analog thereof; and administering a therapeutically effective amount of the retinoid agonist and the G-CSF or the analog thereof to the subject, thereby treating, preventing, reducing the likelihood of developing, reducing the severity of, promoting prophylaxis of and/or slowing the progression of the condition in the subject. In various embodiments, the retinoid agonist and the G-CSF or the analog thereof are in one composition. In other embodiments, the retinoid agonist and the G-CSF or the analog thereof are in separate compositions. In an embodiment, neutropenia is cancer chemotherapy induced neutropenia (CCIN).

In various embodiments, infectious diseases are caused by infectious bacteria. Examples of infectious bacteria include: *Helicobacterpyloris, Borelia burgdorferi, Legionella pneumophilia, Mycobacteria* sps (such as *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira,* and *Actinomyces israelli*. The compositions and methods described herein are contemplated for use in treating infections with these bacterial agents. Other infectious organisms (such as protists) include: *Plasmodium falciparum* and *Toxoplasma gondii*. The compositions and methods described herein are contemplated for use in treating infections with these agents.

In various embodiments, infectious diseases may be caused by viral infections. Examples of infectious viruses include: Retroviridae (for example, HIV); Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that may be treated with the compositions and methods described herein include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans,* and *Aspergillus* spp. The compositions and methods described herein are contemplated for use in treating infections with these fungal agents.

In various embodiments, the subject is a human. In various embodiments, the subject is a mammalian subject including but not limited to human, monkey, ape, dog, cat, cow, horse, goat, pig, rabbit, mouse and rat. In some embodiments, the subject has consistent microbial infection including but not limited to bacterial, viral, fungal and parasitic infections.

In various embodiments, the retinoid agonist is tamibarotene (Am80, retinobenzoic acid, AMNOID, TAMIBARO), CH55, ITYA (ITYA-01115), Am580, BD4, or NRX195183 (also referred to as AGN195183), or their functional equivalents, analogs, or derivatives, or a combination thereof. In various embodiments, the retinoid agonist is a RARα-specific agonist. In an embodiment, the retinoid agonist is Am80, or a functional equivalent, analog, derivative or salt of Am80.

In various embodiments, the G-CSF or the analog thereof can be from any source, e.g., rat, mouse, guinea pig, dog, cat, rabbit, pig, cow, horse, goat, donkey or human. In accordance with the invention, examples of the G-CSF or the analog thereof include but are not limited to a wild type G-CSF, a recombinant G-CSF, a G-CSF monomer or dimer, a recombinant human G-CSF (rhG-CSF) dimer, a G-CSF mutant, a G-CSF fusion protein, a G-CSF fragment, a modified G-CSF polypeptide, a PEGylated G-CSF, a glycosylated G-CSF, and a G-CSF modified with Y-shaped branched polyethylene glycol (YPEG-G-CSF) at a specific lysine (Lys 17). These various G-CSFs and G-CSF equivalents, analogs, derivatives, variants or fragments are functional molecules that possess a biological activity substantially similar to or even better than wild type G-CSFs. Additional information can be found in, for example, U.S. Pat. No. 8,557,546 (Recombinant human G-CSF dimer and use thereof for the treatment of neurological diseases); U.S. Pat. No. 8,530,417 (Y-shaped polyethylene glycol modified G-CSF, the preparation and use thereof); U.S. Pat. No. 8,507,221 (Process for the expression of peptides of interest using GCSF as a fusion partner); U.S. Pat. No. 8,058,398 (Modified G-CSF polypeptide); U.S. Pat. No. 7,655,766 (Compositions comprising positional isomers of PEGylated G-CSF); and U.S. Pat. No. 7,402,304 (Methods of using G-CSF analog compositions), which are incorporated herein by reference in their entirety as though fully set forth.

Typical dosages of an effective amount of the retinoid agonist or the G-CSF or the analog thereof can be in the ranges recommended by the manufacturer where known therapeutic compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the retinoid agonist or the G-CSF or the analog thereof may be administered once a day (SID/QD), twice a day (BID), three times a day (TID), four times a day (QID), or more, so as to administer an effective amount of the retinoid agonist and the G-CSF or the analog thereof to the subject, where the effective amount is any one or more of the doses described herein.

In various embodiments, the retinoid agonist is administered at about 0.001 to 0.01 mg/kg, 0.01 to 0.1 mg/kg, 0.1 to 0.5 mg/kg, 0.5 to 5 mg/kg, 5 to 10 mg/kg, 10 to 20 mg/kg, 20 to 50 mg/kg, 50 to 100 mg/kg, 100 to 200 mg/kg, 200 to 300 mg/kg, 300 to 400 mg/kg, 400 to 500 mg/kg, 500 to 600 mg/kg, 600 to 700 mg/kg, 700 to 800 mg/kg, 800 to 900 mg/kg, or 900 to 1000 mg/kg. In some embodiments, the retinoid agonist is administered 1-3 times per day or 1-7 times per week. Still some embodiments, the retinoid agonist is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In an embodiment, the retinoid agonist is Am80, or a functional equivalent, analog, derivative or salt of Am80. Here, "mg/kg" refers to mg per kg body weight of the subject. In certain embodiments, the retinoid agonist is administered to a human.

In various embodiments, the effective amount of the retinoid agonist is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Here, "µg/kg/day" or "mg/kg/day" refers to µg or mg per kg body weight of the subject per day.

In various embodiments, the G-CSF or the analog thereof is administered at about 0.01 to 0.1 mcg/kg, 0.1 to 0.5 mcg/kg, 0.5 to 5 mcg/kg, 5 to 10 mcg/kg, 10 to 20 mcg/kg, 20 to 50 mcg/kg, 50 to 100 mcg/kg, 100 to 200 mcg/kg, 200 to 300 mcg/kg, 300 to 400 mcg/kg, 400 to 500 mcg/kg, 500 to 600 mcg/kg, 600 to 700 mcg/kg, 700 to 800 mcg/kg, 800 to 900 mcg/kg, or 900 to 1000 mcg/kg. In some embodiments, the G-CSF or the analog thereof is administered 1-3 times per day or 1-7 times per week. Still in some embodiments, the G-CSF or the analog thereof is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mcg/kg" refers to mcg per kg body weight of the subject. In certain embodiments, the G-CSF or the analog thereof is administered to a human.

In various embodiments, regimen doses may be converted between mouse and human. Table 1 provides an exemplar chart of conversions. As a non-limiting example, for clinical treatment of APL patients who had relapsed after ATRA-induced complete remissions (CRs), the patients receive 6 to 9 mg/m$^2$ Am80 daily (oral) for maximum 56 days without interval. As further non-limiting examples, neutropenia (congenital, idiopathic or cyclic) patients receive 0.5-40 mcg/kg/day G-CSF via subcutaneous injection, and chemotherapy-induced neutropenia patients receive 4-69 mcg/kg/day (7-20 days) G-CSF via subcutaneous injection.

TABLE 1

| In some embodiments, conversion of Regimen Doses between Mouse and Human | | | |
|---|---|---|---|
| Am80 | | G-CSF | |
| Mice | Human | Mice | Human |
| 0.5 mg/kg | 1.5 mg/m$^2$ or 0.04 mg/kg | 25 mcg/kg | 76.0125 mcg/m$^2$ or 2.027 mcg/kg |
| 1.0 mg/kg | 3 mg/m$^2$ or 0.08 mg/kg | 50 mcg/kg | 152.025 mcg/m$^2$ or 4.054 mcg/kg |
| 5.0 mg/kg | 15 mg/m$^2$ or 0.4 mg/kg | 250 mcg/kg | 760.125 mcg/m$^2$ or 20.27 mcg/kg |

In some embodiments, the retinoid agonist and the G-CSF or the analog thereof may be administered at neutrophil-decrease stage of a condition (i.e., when the subject has not developed the condition but is likely to or in the process to develop the condition). In other embodiments, the retinoid agonist and the G-CSF or the analog thereof may be administered at the treatment stage of a condition (i.e., when the subject has already developed the condition). As a non-limiting example, the target condition is neutropenia and the subject is a cancer patient who has been prescribed with a chemotherapy or radiotherapy. In this exemplar situation, the patient may be treated with the methods described herein when the patient has not yet developed neutropenia, or is in the process of developing neutropenia, or has already developed neutropenia.

In accordance with the invention, the retinoid agonist and the G-CSF or the analog thereof may be administered using the appropriate modes of administration, for instance, the modes of administration recommended by the manufacturer for each of the retinoid agonist and the G-CSF or the analog thereof. In accordance with the invention, various routes may be utilized to administer the retinoid agonist and the G-CSF or the analog thereof of the claimed methods, including but not limited to aerosol, nasal, oral, transmucosal, transdermal, parenteral, implantable pump, continuous infusion, topical application, capsules and/or injections. In various embodiments, the retinoid agonist is administered intravenously, intramuscularly, subcutaneously, intraperitoneally, orally or via inhalation. In various embodiments, the G-CSF or the analog thereof is administered intravenously, intramuscularly, subcutaneously, intraperitoneally, orally or via inhalation. The retinoid agonist and the G-CSF or the analog thereof may be administered via the same or separate routes.

In various embodiments, the retinoid agonist and the G-CSF or the analog thereof are administered concurrently or sequentially. In various embodiments, the retinoid agonist is administered before, during or after administering the G-CSF or the analog thereof. In further embodiments, the retinoid agonist and/or the G-CSF or the analog thereof are administered with food or without food. As a non-limiting example, the retinoid agonist (e.g., Am80) may be administered, for example, daily at the aforementioned dosages, and the G-CSF or the analog thereof may be administered, for example, daily, weekly, biweekly, every fortnight and/or monthly at the aforementioned dosages. As another non-limiting example, the retinoid agonist may be administered, for example, daily, weekly, biweekly, every fortnight and/or monthly, at the aforementioned dosages, and the G-CSF or the analog thereof may be administered, for example, daily at the aforementioned dosages. Further, each of the retinoid agonist and the G-CSF or the analog thereof may be administered daily, weekly, biweekly, every fortnight and/or monthly, wherein the retinoid agonist is administered at the aforementioned dosages on a day different than the day on which the G-CSF or the analog thereof is administered at the aforementioned dosages.

In various embodiments, the method may further comprise providing and administering a chemotherapeutic to the subject. In accordance with the invention, the retinoid agonist, the G-CSF or the analog thereof, and the chemotherapeutic are administered concurrently or sequentially. Still in accordance with the invention, the retinoid agonist and/or the G-CSF or the analog is administered before, during or after administering the chemotherapeutic. In some embodiments, the retinoid agonist, the G-CSF or the analog thereof, and the chemotherapeutic are in one composition or separate compositions.

Examples of chemotherapeutic agents include but are not limited to Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

In various embodiments, the method may further comprise providing and administering an antimicrobial agent to the subject. In accordance with the invention, the retinoid agonist, the G-CSF or the analog thereof, and the antimicrobial agent are administered concurrently or sequentially. Still in accordance with the invention, the retinoid agonist and/or the G-CSF or the analog is administered before, during or after administering the antimicrobial agent. In some embodiments, the retinoid agonist, the G-CSF or the analog thereof, and the antimicrobial agent are in one composition or separate compositions. The antimicrobial agent may be an antibacterial, antiviral, antifungal, or antiparasitic agent, or a combination thereof.

Pharmaceutical Compositions

In various embodiments, the present invention provides compositions comprising a retinoid agonist and a G-CSF or an analog thereof. In one embodiment, the retinoid agonist and G-CSF are in the same composition. In another embodiment, the retinoid againist and G-CSF are in separate compositions. In accordance with the present invention, the compositions may be used for treating, preventing, reducing the likelihood of having, reducing the severity of and/or slowing the progression of a condition in a subject. In accordance with the invention, the condition may be neutropenia or microbial infection. Still in accordance with the present invention the compositions may be used for stimulating a cell (including but not limited to a HSC, a bone marrow granulocytic progenitor cell, and a hematopoietic CD34+ cell) to generate granulocytes, and particularly, neutrophils.

In various embodiments, the retinoid agonist is tamibarotene (AM 80, retinobenzoic acid, Amnoid, Tamibaro), CH55, ITYA (ITYA-01115), Am580, BD4, or NRX195183 (also referred to as AGN195183), or their functional equivalents, analogs, or derivatives, or a combination thereof. In various embodiments, the retinoid agonist is a RARα-specific agonist. In an embodiment, the retinoid agonist is Am80, or a functional equivalent, analog, derivative or salt of Am80.

In various embodiments, the retinoid agonist in the composition is provided in a mg per kilogram weight of the subject; for example, about 0.001 to 0.01 mg/kg, 0.01 to 0.1 mg/kg, 0.1 to 0.5 mg/kg, 0.5 to 5 mg/kg, 5 to 10 mg/kg, 10 to 20 mg/kg, 20 to 50 mg/kg, 50 to 100 mg/kg, 100 to 200 mg/kg, 200 to 300 mg/kg, 300 to 400 mg/kg, 400 to 500 mg/kg, 500 to 600 mg/kg, 600 to 700 mg/kg, 700 to 800 mg/kg, 800 to 900 mg/kg, or 900 to 1000 mg/kg. In an embodiment, the retinoid agonist is Am80, or a functional equivalent, analog, derivative or salt of Am80. In certain embodiments, the composition is administered to a human.

In various embodiments, the G-CSF or the analog thereof in the composition is provided in a mcg per kg weight of the subject; for example, about 0.01 to 0.1 mcg/kg, 0.1 to 0.5 mcg/kg, 0.5 to 5 mcg/kg, 5 to 10 mcg/kg, 10 to 20 mcg/kg, 20 to 50 mcg/kg, 50 to 100 mcg/kg, 100 to 200 mcg/kg, 200 to 300 mcg/kg, 300 to 400 mcg/kg, 400 to 500 mcg/kg, 500 to 600 mcg/kg, 600 to 700 mcg/kg, 700 to 800 mcg/kg, 800 to 900 mcg/kg, or 900 to 1000 mcg/kg. In certain embodiments, the composition is administered to a human.

In one embodiment, the compositions further comprise a chemotherapeutic. In another embodiment, the compositions furthers comprise an antimicrobial agent. In various embodiments, the compositions are formulated for intravenous, intramuscular, subcutaneous, intraperitoneal, oral or via inhalation administration.

In accordance with the invention, the retinoid agonist and/or the G-CSF or the analog thereof useful in the treatment of disease in mammals will often be prepared substantially free of naturally-occurring immunoglobulins or other biological molecules. Preferred retinoid agonists and/or G-CSFs or analogs thereof will also exhibit minimal toxicity when administered to a mammal.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

In various embodiments, the composition is administered 1-3 times per day or 1-7 times per week. In various embodiments, the composition is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In accordance with the invention, the composition may be formulated for intravenous, intramuscular, subcutaneous, intraperitoneal, oral or via inhalation administration. In various embodiments, the composition may be administered once a day (SID/QD), twice a day (BID), three times a day (TID), four times a day (QID), or more, so as to administer an effective amount of the retinoid agonist and the G-CSF or the analog thereof to the subject, where the effective amount is any one or more of the doses described herein.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., *Drug Delivery Systems* (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Cell Therapies

In various embodiments, the present invention provides a method of generating granulocytes, and in particular, neutrophils. The method comprises: providing a cell (including but not limited to a HSC, a bone marrow granulocytic progenitor cell, and a hematopoietic $CD34^+$ cell); and stimulating the cell with a retinoid agonist and a G-CSF or an analog thereof, thereby generating granulocytes, and in particular, neutrophils. In accordance with the invention, the method may further comprise culturing the stimulated cell and/or the generated granulocytes, and in particular, neutrophils. In accordance with various embodiments of the invention, the method further comprises isolating the stimulated cell and/or the generated granulocytes, and in particular, neutrophils. In accordance with various embodiments of the invention, the method further comprises administering the stimulated cell and/or the generated granulocytes, and in particular, neutrophils to a subject who desires a treatment of a condition. In various embodiments, the invention provides a kit of generating granulocytes, and in particular, neutrophils. The kit comprises: a quantify of a retinoid agonist; a quantify of G-CSF or an analog thereof; and instructions for using the retinoid agonist and the G-CSF or the analog thereof to stimulate a cell (including but not limited to a HSC, a bone marrow granulocytic progenitor cell, and a hematopoietic $CD34^+$ cell) to generate granulocytes, and in particular, neutrophils.

In various embodiments, the invention provides a composition comprising the generated granulocytes, or in particular, neutrophils according to the described method and/or using the described kit. In various embodiments, the invention provides a composition comprising the stimulated cell according to the described method and/or using the described kit. In accordance with various embodiments of the present invention, these compositions further comprise a retinoid agonist and a G-CSF or an analog thereof. In accordance with various embodiments of the present invention, these compositions further comprise a pharmaceutically acceptable excipient and/or carrier. In accordance with the present invention, these compositions may be formulated for administration to a subject via various routes including but not limited to transfusion and transplantation. In further embodiments, the invention provides a method of treating, preventing, reducing the severity of and/or slowing the progression of a condition in a subject by administering at least one of these described compositions to the subject. As a non-limiting example, the subject may be a patient with neutropenia, and a composition comprising the generated granulocytes, or in particular, neutrophils may be transfused into the patient. As another non-limiting example, the subject may be an AML patient, and a composition comprising the stimulated HSCs and/or bone marrow cells may be transplanted to the patient.

In various embodiments, the present invention provides a method of treating, preventing, reducing the likelihood of having, reducing the severity of and/or slowing the progression of a condition in a subject. The method comprises: providing a cell (including but not limited to a HSC, a bone marrow granulocytic progenitor cell, and a hematopoietic $CD34^+$ cell); stimulating the cell with a retinoid agonist and a G-CSF or an analog thereof, thereby generating granulocytes, or in particular, neutrophils; and administering the generated granulocytes, or in particular, neutrophils to the subject, thereby treating the condition in the subject. In various embodiments, the condition is neutropenia or AML. In various embodiments, the generated granulocytes, or in particular, neutrophils are administered to the subject via transfusion or transplantation.

In various embodiments, the present invention provides a method of treating, preventing, reducing the likelihood of having, reducing the severity of and/or slowing the progression of a condition in a subject. The method comprises: providing a cell (including but not limited to a HSC, a bone marrow cell, a $CD34^+$ cell, and a stem cell); stimulating the cell with a retinoid agonist and a G-CSF or an analog thereof; and administering the stimulated cell to the subject, thereby treating the condition in the subject. In various embodiments, the condition is neutropenia or AML. In various embodiments, the stimulated cell is administered to the subject via transfusion or transplantation.

Kits of the Invention

In various embodiments, the present invention provides a kit for treating, preventing, reducing the severity of and/or slowing the progression of a condition in a subject. The kit comprises: a quantify of a retinoid agonist; a quantify of G-CSF or an analog thereof; and instructions for using the retinoid agonist and the G-CSF or the analog thereof to treat, prevent, reduce the severity of and/or slow the progression of the condition in the subject.

In various embodiments, the retinoid agonist is tamibarotene (Am80, retinobenzoic acid, Amnoid, Tamibaro), CH55, ITYA (ITYA-01115), Am580, BD4, or NRX195183 (also referred to as AGN195183), or their functional equivalents, analogs, or derivatives, or a combination thereof. In various embodiments, the retinoid agonist is a RARα-specific agonist. In an embodiment, the retinoid agonist is Am80, or a functional equivalent, analog, derivative or salt of Am80.

In various embodiments, the G-CSF or the analog thereof can be from any source, e.g., rat, mouse, guinea pig, dog, cat, rabbit, pig, cow, horse, goat, donkey or human. In accordance with the invention, examples of the G-CSF or the analog thereof include but are not limited to a wild type G-CSF, a recombinant G-CSF, a G-CSF monomer or dimer, a recombinant human G-CSF (rhG-CSF) dimer, a G-CSF mutant, a G-CSF fusion protein, a G-CSF fragment, a modified G-CSF polypeptide, a PEGylated G-CSF, a glycosylated G-CSF, and a G-CSF modified with Y-shaped branched polyethylene glycol (YPEG-G-CSF) at a specific lysine (Lys 17). These various G-CSFs and G-CSF equivalents, analogs, derivatives, variants or fragments are functional molecules that possess a biological activity substantially similar to or even better than wild type G-CSFs. Additional information can be found in, for example, U.S. Pat. No. 8,557,546 (Recombinant human G-CSF dimer and use thereof for the treatment of neurological diseases); U.S. Pat. No. 8,530,417 (Y-shaped polyethylene glycol modified G-CSF, the preparation and use thereof); U.S. Pat. No. 8,507,221 (Process for the expression of peptides of interest using GCSF as a fusion partner); U.S. Pat. No. 8,058,398 (Modified G-CSF polypeptide); U.S. Pat. No. 7,655,766 (Compositions comprising positional isomers of PEGylated G-CSF); and U.S. Pat. No. 7,402,304 (Methods of using G-CSF analog compositions), which are incorporated herein by reference in their entirety as though fully set forth.

The kit is an assemblage of materials or components, including at least one of the inventive compositions. Thus, in some embodiments the kit contains a composition including a drug delivery molecule complexed with a therapeutic agent, as described above.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

In some embodiments, the subjects in need of the methods, compositions, and kits described herein are subjects with decreased white blood cell production resulting from, including but not limited to, medication that affects the bone marrow (such as cancer drugs, antipsychotic drugs, anticonvulsant drugs), hereditary and/or congenital disorders that affect the bone marrow, patients undergoing radiation therapy, vitamin B12 deficiency, folic acid deficiency or a combination thereof.

In further embodiments, the subjects in need of the methods, compositions, and kits described herein are subjects with damaged, destroyed and/or reduced amounts of white blood cells due to, including but not limited to, acute bacterial infections, autoimmune disorders (such as systemic lupus erythematosus), use of sulfonamide medications, or a combination thereof.

In additional embodiments, the subjects in need of the methods, compositions, and kits described herein are subjects undergoing sequestration and/or migration of white blood cells (such as neutrophils) due to, including but not limited to, hemodialysis, malaria, bacterial infections or a combination thereof.

In various embodiments, the methods, compositions, and kits described herein may be used in conjunction with other therapies including but not limited to chemotherapy and/or radiation therapy. Chemotherapy and/or radiation therapy often reduce the number of white blood cells, resulting in neutropenia. Applying the methods, compositions, and kits of the invention concurrently or sequentially with the chemotherapy and/or radiation therapy may prevent, inhibit and/or reduce the severity of neutropenia. Similarly, applying the methods, compositions, and kits of the invention concurrently or sequentially with anticonvulsant and/or antipsychotic drugs may prevent, inhibit and/or reduce the severity of neutropenia resulting from the use of said drugs. Additionally, applying the methods, compositions, and kits of the invention concurrently or sequentially with therapeutic agents used to treat microbial infections (e.g., bacterial, fungal, viral and parasitic infections) and/or autoimmune diseases or radiation-induced neutropenia may prevent, inhibit and/or reduce the severity of neutropenia that may occur due to microbial infections and/or autoimmune diseases and/or due to the therapeutic agents that may be used to treat microbial infections and/or autoimmune diseases.

Methods for Assessing Treatment Efficacy

As described herein, using lower-than-approved doses of Am80 in combination with GCSF, the infection-related mortality of neutropenic mice was markedly reduced compared to Am80 or GCSF alone. Moreover, Am80 treatment in combination with GCSF in both normal and malignant hematopoietic precursors increased reactive oxygen species (ROS) production, an essential neutrophil function in fighting microbial infection. ROS production bioassays may be used to assess efficacy of combination treatment methods described herein, based on neutrophil microbicidal function against both bacterial and fungal infections. Current clinical endpoints for neutropenia therapy include neutrophil counts and the incidence of febrile neutropenia, neither of which provide information on the neutrophils' ability to fight microorganisms. The ROS production bioassay permits monitoring of neutrophil microbicidal activity based on reference values of neutrophil ROS production in response to either bacterial or fungal stimuli. Such established baseline values of neutrophil ROS production deliver a rapid functional clinical endpoint critical to identifying the optimal dosing and schedule of Am80 as an add-on therapy to GCSF.

Accordingly, provided herein are methods for determining the efficacy of treatment in a subject in need thereof. The methods include providing a sample from a subject, wherein the subject has been administered an effective a retinoid agonist and an effective amount of G-CSF, assaying the levels production of reactive oxygen species (ROS) and determining that the treatment is efficacious if the ROS production is higher than that of a reference sample or determining that the treatment is not efficacious if the ROS production is same as the reference sample or lower relative to the reference sample. In some embodiments, if the treatment is not deemed efficacious, the dose of Am80 or GCSF or both may be increased.

In some embodiments, the subject in whom the efficacy is to be evaluated is undergoing chemotherapy treatment or has undergone chemotherapy treatment (with or without GCSF. In some embodiments, the subject in whom the efficacy is to be evaluated is undergoing treatment for neutropenia or has undergone treatment of neutropenia.

In one embodiment, the sample is blood, peripheral blood, bone marrow cells, plasma, tissue or a combination thereof. In various embodiments, the sample is obtained before, during or after treatment for neutropenia. In exemplary embodiments, ROS production may be determined as described in Babior, *Blood* 1999, vol. 93, page: 1464; Dahlgren et al., *J Immunol Methods*, 1999, Vol. 232, Page: 3; Weiss, *Acta Physiol Scand Suppl*, 1986, Vol. 548, page: 9; Charles et al., *Infect Immun*, 2008, Vol. 76, page: 2439; Wei et al., *J Biomed Opt*, 2010, vol. 15, page: 027006. In some embodiments, ROS production is measured using stimulators that mimic bacterial and fungal infections, for example fMLP, PMA, ZAS or a combination thereof.

In various embodiments of the methods described herein, the reference value is based on the amount/level of production of reactive oxygen species (ROS). In one embodiment, the reference value is based on the ROS production in bone marrow cells from healthy donors. In another embodiment, the reference value is based on the ROS production in peripheral blood mononuclear cell from healthy donors. In an additional embodiment, the reference value is based on the ROS production in healthy bone marrow cells from subjects that have or had acute myeloid leukemia. In a further embodiment, the reference value is based on the ROS production in healthy peripheral blood cells from subjects that have or had acute myeloid leukemia. (What other cell types? Any broader embodiments?) Other cell types that may be used to determine the reference value will be apparent to a person of skill in the art. In additional embodiments, the reference value is the amount/level of ROS production in a sample obtained from the subject from a different (for example, an earlier) time point, such as during diagnosis of neutropenia, before treatment of neturopenia, after treatment for neutropenia or a combination thereof.

In various embodiments, the amount/level of ROS production in the subject (for example, the subject that is being treated for neutropenia) compared to the reference value is increased by at least or about 10%, 20%, 30%, 40%, 50%, 60%, 70%, 80%, 90% or 100%. In various embodiments, the amount/level of ROS production in the subject (for example, the subject that is being treated for neutropenia) compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

EXAMPLES

The following examples are offered for illustrative purposes only, and are not intended to limit the scope of the present invention in any way.

Example 1: Myelopoietic Expansion Vs. Myeloipoietic Differentiation Induced by Selective Activity of Am80

What are the mechanisms underlying the synergistic effect of Am80-GCSF on regeneration of mature neutrophils to reduce mortality of neutropenic mice exposed to bacteria? Cell-specific transcription patterns can be altered by modulating transcription factors, the master regulators of cell fate. All-trans retinoic acid (ATRA or RA) has high affinity binding to and transactivation of two classes of transcription factors, retinoic acid receptors (RARα, -β, -γ) and retinoid X receptors (RXRα, -β, -γ). Previous studies show that RA enhances HSC self-renewal through RARγ activation while promoting differentiation of committed myeloid progenitors through RARα activation. Such pan-action of RA exerts potent effects on inhibiting proliferation while promoting differentiation by activating RARα, -β, -γ subtypes in various normal and tumor tissues. By contrast, Am80 is a retinoid agonist designed to selectively binding RARα but not RARγ thus avoiding the side effects induced by RA-activated RARγ in the treatment of APL patients. We demonstrate that Am80 promotes a modest myeloid expansion while significantly enhancing differentiation of neutrophils against bacterial infection, which is in contrast to G-CSF that profoundly enhances myeloid expansion while failing to induce effective neutrophil differentiation. The discovery, a combined Am80-GCSF treatment is significantly greater than Am80 to markedly reduces mortality of neutropenic mice in the presence of consistent bacterial infection, suggests that although the selective activation of RARα by Am80 can contribute to effective neutrophil differentiation, Am80-mediated modest myeloid expansion does not meet the demand for sufficient numbers of mature neutrophils in the context of consistent bacterial infection coinciding with neutropenia. These findings indicate a need to use combined Am80-GSCF to sufficiently balance both myeloid expansion and neutrophil differentiation, thereby overcoming the ineffectiveness resulting from current G-CSF therapy for treatment of cancer chemotherapy-induced neutropenia.

Example 2: Signaling Pathway Modulating the Synergistic Effect of Am80-G-CSF

Figure 2:
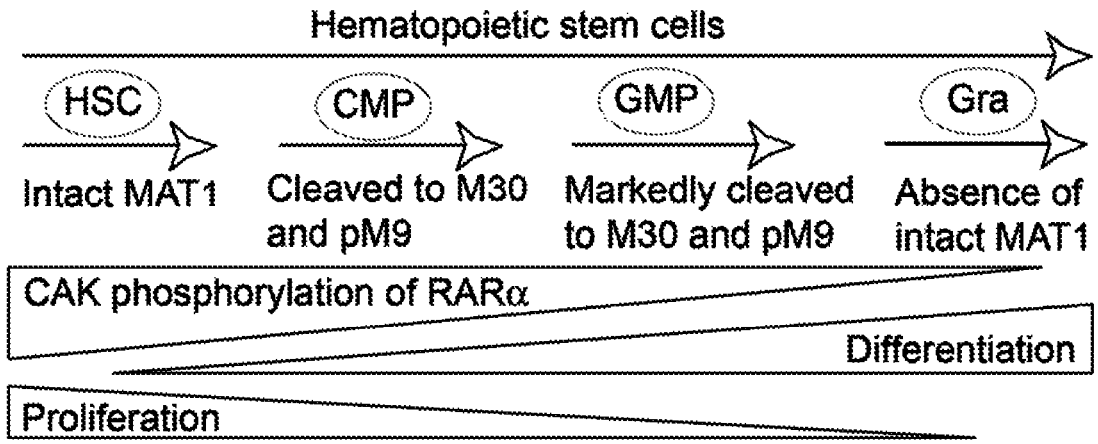
FIG. 2 depicts, in accordance with various embodiments of the invention, intrinsically programmed cleavage of MATT protein into M30 and pM9 fragments decreases CAK phosphorylation of RARα, leading to granulopoiesis underlying balanced myelopoietic expansion and differentiation. CMP: common myeloid progenitors; GMP: granulocyte/monocyte progenitors; and Gra: granulocytes.
Figure 3:
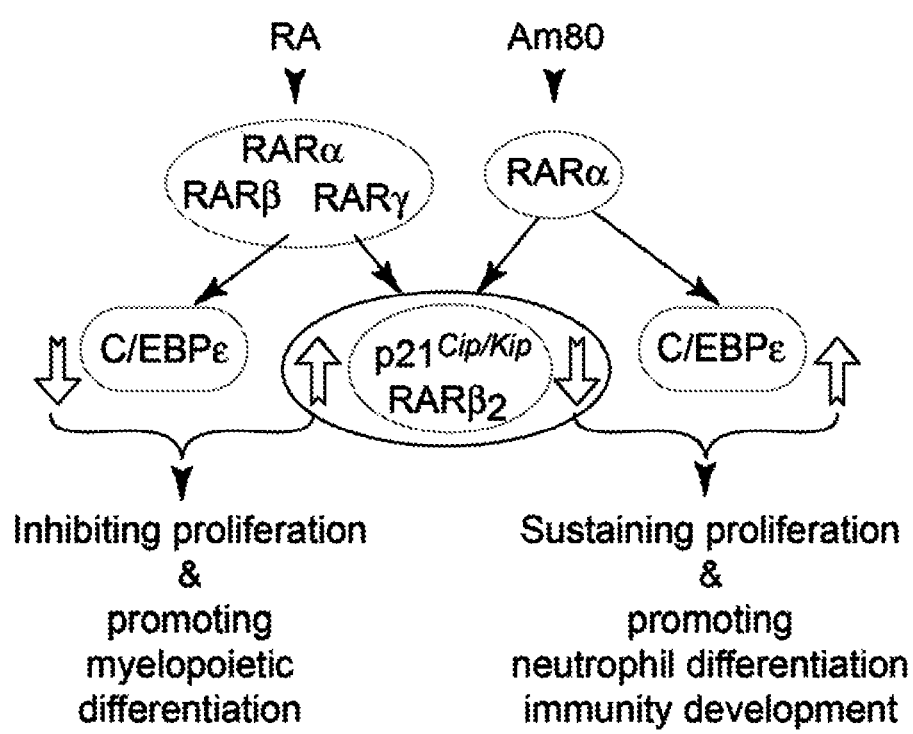
FIG. 3 depicts, in accordance with various embodiments of the invention, as compared to RA, Am80 selectively activates RARα to induce a novel transcription response for stimulating both myeloid expansion and differentiation. Ribbon up-arrow indicates increased expression and ribbon down-arrow indicates decreased expression.

RARα is a substrate for cyclin-dependent kinase-activating kinase (CAK) complexes consisting of CDK7, cyclin H, and MAT1 proteins. CAK exists in cells either as a free CAK to regulate cell cycle progression by phosphorylation-activation of different CDKs, or as a kinase subunit of the TFIIH complex where it mediates transcription through phosphorylation of the RNA polymerase II C-terminal domain (RNA PII). Of note, either free CAK or TFIIH-containing CAK phosphorylates RARα to inhibit granulocytic differentiation (FIG. 1), whereas decrease in CAK phosphorylation of RARα mediated by either intrinsically programmed or RA-mediated MAT1 protein fragmentation induces granulocytic differentiation through RARα-dependent transcription of RA target genes (FIG. 2). We recently discovered that Am80 effect arises from its selective activation of RARα transcription factor to induce selective expression of RA target genes by inhibiting CAK phosphorylation of RARα. Am80-induced myelopoietic expansion underlies an altered transcription expression pattern of RA target genes, as shown by decreased levels of cell cycle inhibitor p21$^{Cip/Kip}$ but increased expression of neutrophil effector CD18, secondary granule LL-37, and the myeloid-specific transcription factor CCAAT/enhancer binding protein-epsilon (C/EBPε). This Am80-induced selective expression of RA target genes is distinct from RA stimuli and is associated with effective development of neutrophil bactericidal functions, significant MAT1 fragmentation, decreased RARα phosphorylation, and markedly higher production of reactive oxygen species (ROS) in either normal or malignant hematopoietic precursors, as compared to G-CSF or RA. These data suggest that through retinoid-mediated CAK-RARα signaling pathway in control of transcription response for granulopoiesis, selective binding of Am80 to RARα induces a novel transcription response to coordinate modest myelopoietic expansion and effective neutrophil differentiation (FIG. 3). Based on these studies together with our discovery that Am80-GCSF combination markedly reduces mortality of neutropenic mice, while not wishing to be bound by a particular theory, we think that the synergistic effect of Am80-GCSF combination may rely on mediating CAK-RARα mode of action, which cross-regulates both optimal expansion of myelopoietic precursors and effective terminal differentiation of neutrophils, leading to reduction of infection and infection-induced mortality. Our studies provide an effective therapy overcoming deficiencies of using single regimens of either Am80 or GCSF to treat cancer chemotherapy-induced neutropenic patients.

Example 3: Neutropenia Induced by Cancer Chemotherapy Drug and Neutrophil Recovery As shown by Ding et al. (*Blood* 2013 Vol 121 page 996), Trillet-Lenoir et al. (Eur J Cancer 1993; Vol 29A (3), page 319), Lalami et al. (Ann Oncol 2006; Vol 17 (3), page 507) and Abdul Rasool Hassan et al. (Asian Pac J Cancer Prev, 2011; Vol 12(6), page 1425), cancer chemotherapy may be used to induce neutropenia. The median duration of severe neutropenia induced by cancer chemotherapy is 3-6 days in human (ANC<0.5×10$^9$/L) and 2-3 days in mouse, whereas GCSF can shorten neutropenic duration in both human and mouse by increasing number of neutrophils (FIG. 4). Our studies divide the 2/3 period of mouse neutropenia as neutrophil-decrease (no regimens can prevent reduction of neutrophils in either human or mouse) and neutrophil-recovery (BM function is still inhibited) stages (FIG. 4, right panel), during which the risk to microbial infections is significantly increased. An entire cycle of neutropenia covers neutropenia induction, neutropenia decrease, neutropenia recovery, and neutrophils return to normal stages (FIG. 4, right panel). The effect of Am80-GCSF combination on reducing mortality of neutropenic mice was tested during a full cycle of mouse neutropenia enduring continual bacteremia condition.

Figure 5:
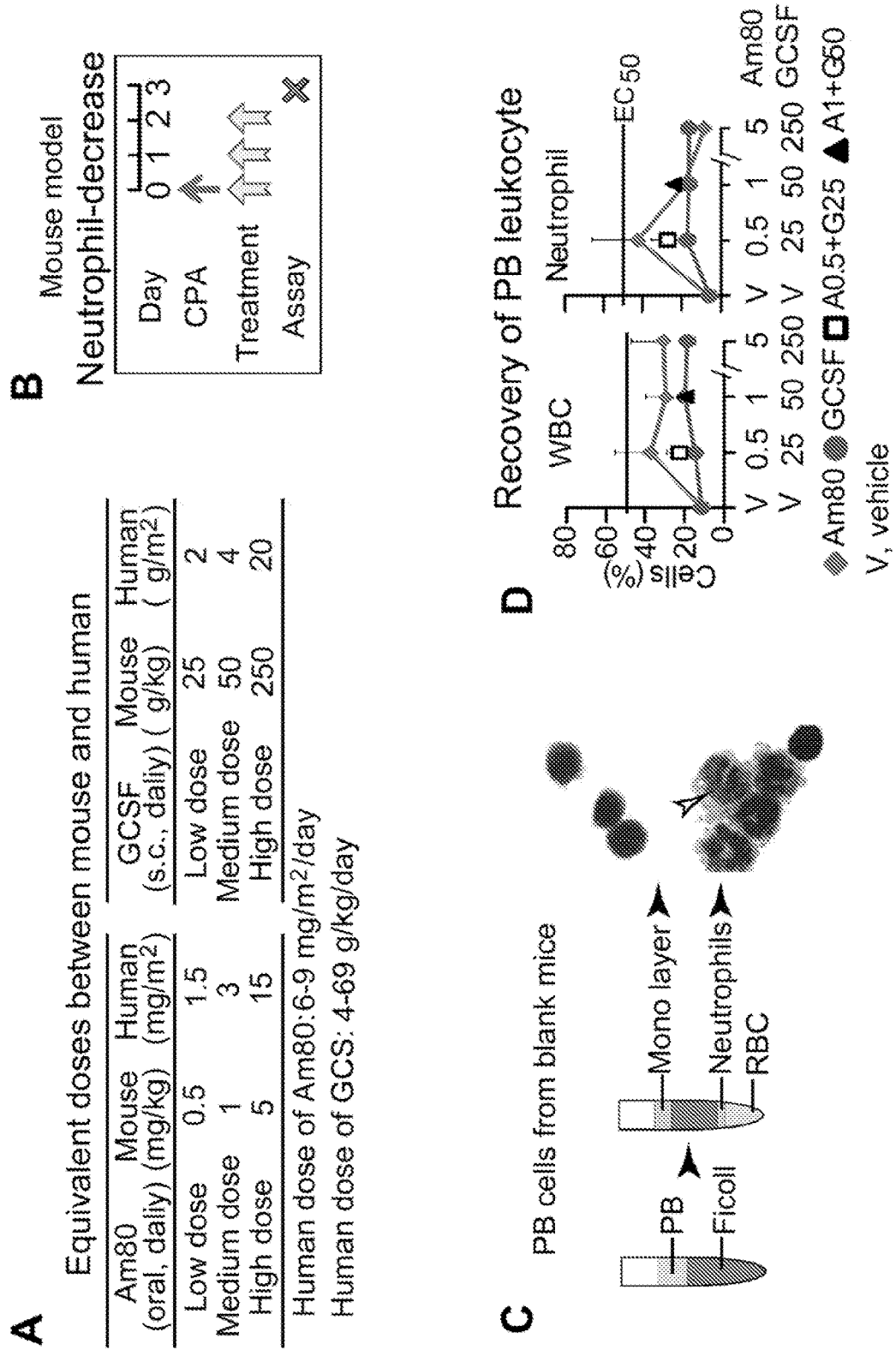
FIG. 5 depicts, in accordance with an embodiment of the invention, $EC_{50}$ test show that human equivalent low and medium doses of Am80 and Am80-GCSF combination effectively promote recovery of neutrophils at neutrophil-decrease stage.
Figure 5:
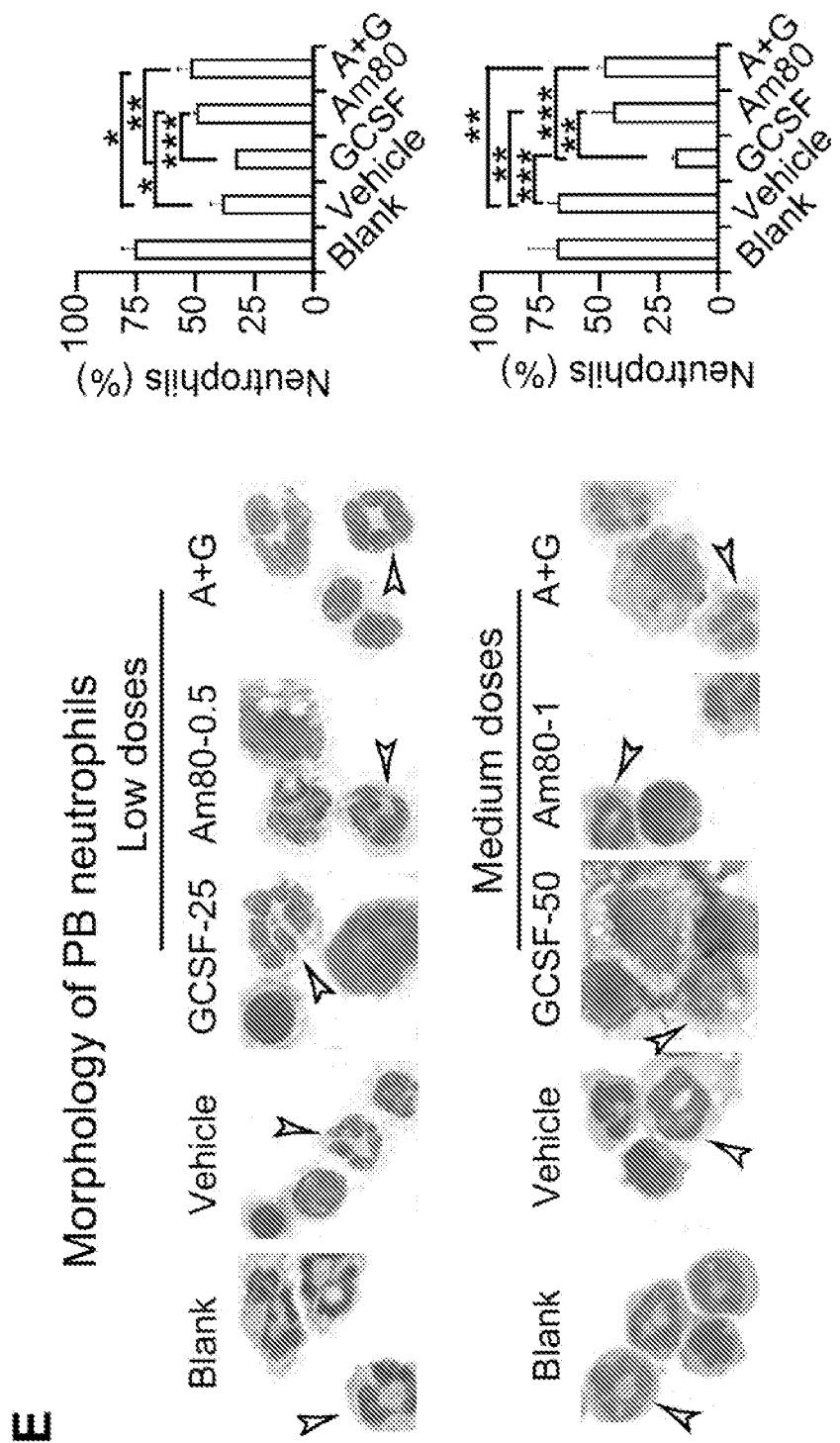
Figure 5:
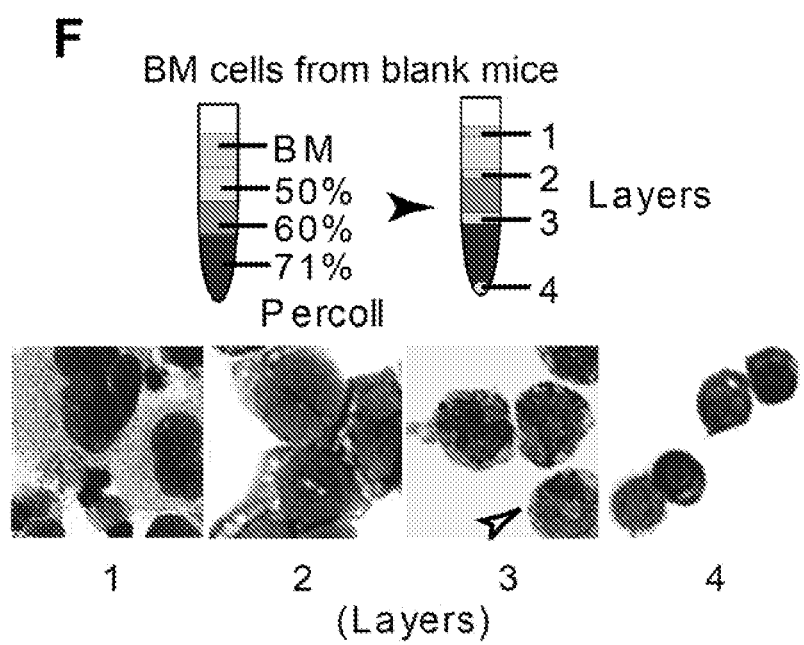
Figure 5:
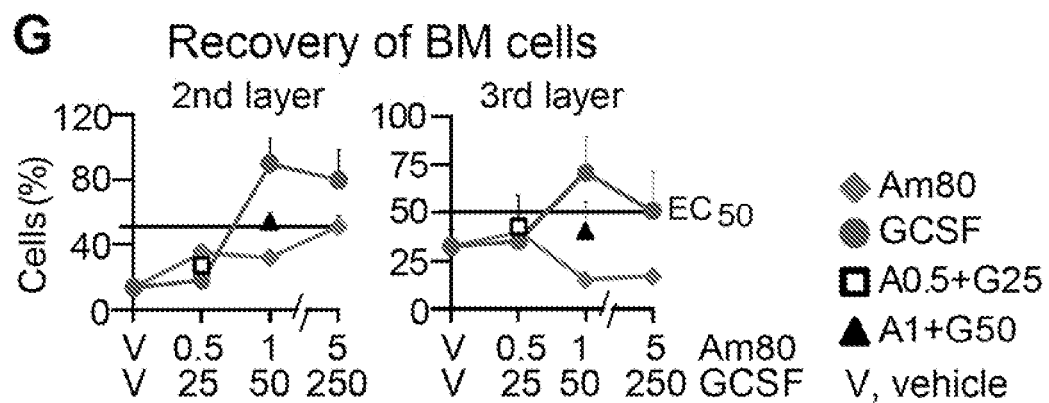
Figure 5:
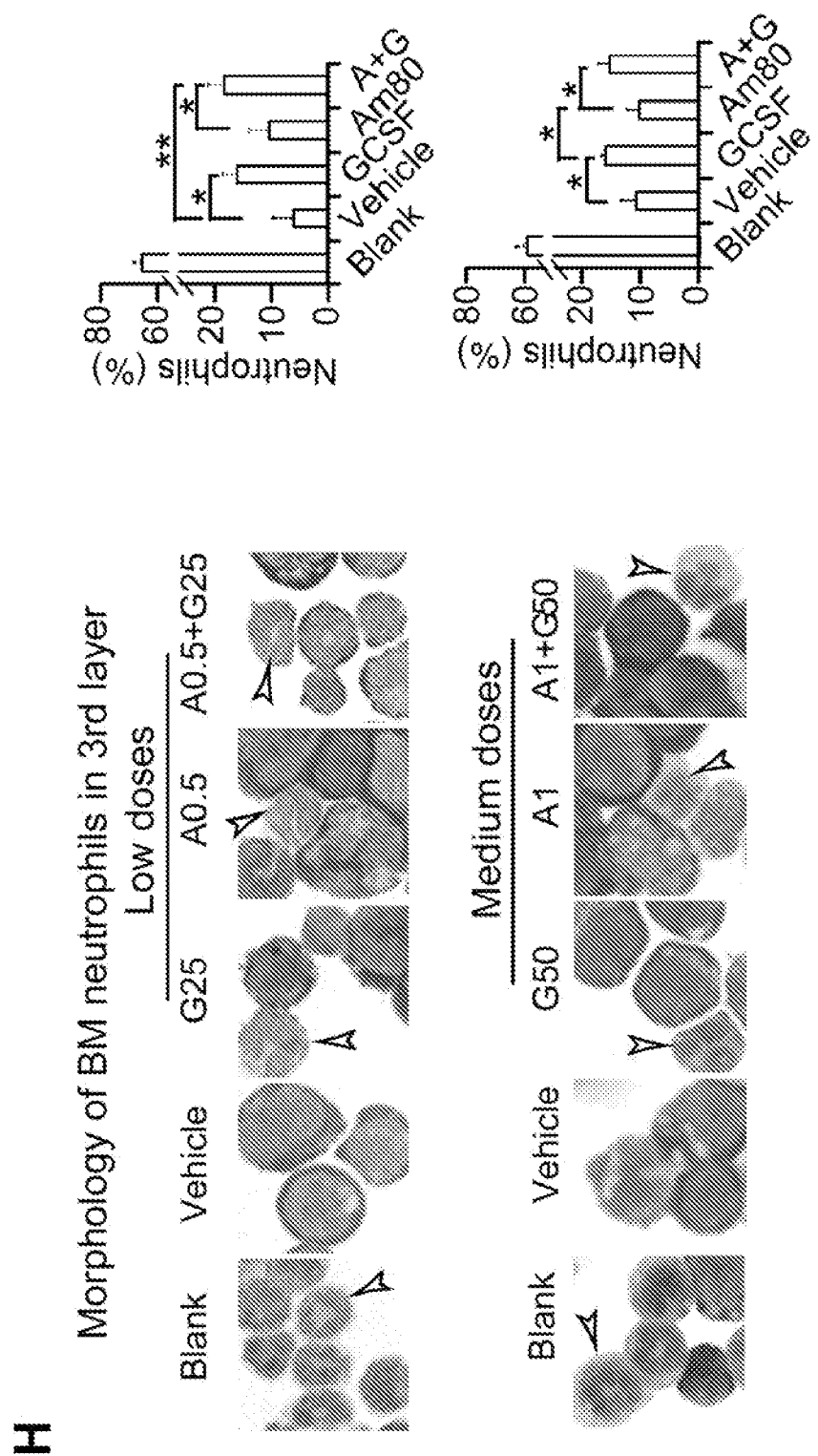

Example 4: Human Equivalent Low and Medium Doses of Am80 and Am80-GCSF Combination Effectively Promote Recovery of Neutrophils at Neutrophil-Decrease Stage To evaluate Am80 effect in vivo, we first tested half maximal effective concentration (EC$_{50}$) of different human equivalent high, medium, and low doses of Am80 and GCSF (FIG. 5a) on regenerating mature neutrophils in neutropenic mice. Normal C57BL6/J mice were injected with a single dose of cyclophosphamide (CPA) to reduce mouse neutrophils. At 4 hr post-injection of CPA, mice were treated with vehicle, Am80, GCSF, or Am80-GCSF for consecutive 3 days before mice were sacrificed (FIG. 5b). Ficoll separation of peripheral blood (PB) of blank mice showed that mature neutrophils were sorted to the lower layer (FIG. 5c). Compared to all other treatments, both low and medium doses of Am80 or Am80-GCSF showed better EC$_{50}$ effect on sustaining neutrophil levels (FIG. 5d, right panel), while low doses of Am80 and Am80-GCSF enhanced granulocytic morphology differentiation better than did medium doses (FIG. 5e). Moreover, multi-density Percoll separation of bone marrow (BM) cells indicated that mature BM neutrophils of blank mice were sorted to the 3$^{rd}$ layer (FIG. 5f). Notably, although medium dose of GCSF induced highest recovery of 3$^{rd}$ layer BM cells (FIG. 5g, right panel), these cells are less differentiated than those induced by low doses of Am80-GCSF, as shown by granulocytic morphologic analysis (FIG. 5h, top vs. bottom panels). Together, these results suggest that low and medium doses of Am80 and Am80-GCSF can sustain moderate levels of both PB and BM neutrophils in early stage of mouse neutropenia. *: P<0.05; : P<0.01; *: P<0.005. Data represent 2 independent experiments with similar results.

Example 5: Neutrophils Induced by Medium Dose of Am80 in Neutropenic Mice at Neutrophil-Decrease Stage Display Greater Bactericidal Activity than Those Induced by G-CSF or Am80-GCSF FIG. 6A experimental design. C57BL/6J mice (n=19) were randomly divided into five groups (3 for control and 4 for each of experimental groups). Mouse neutropenia was induced by IP injection of CPA on day 0. After 4 hrs of CPA injection, different regimens were given to mice once a day, with Am80 by oral or GCSF by SC or vehicle by oral. Mice were challenged by 6.3×10$^6$ CFU of *S. aureus* on day 2 via tail vein injection. After 3 hrs infection, each 100 μl blood was collected from tails for analysis of initial bactericidal activity of neutrophils. The mice were sacrificed 16 hrs post-infection, by which PB and heart were harvested. (FIG. 6B) Vetscan analysis of WBC and neutrophils in PB. Except blank mice, neutrophil induction was not observed in all other groups (FIG. 6C-E). Bactericidal activities of neutrophils were determined 3 hr (FIG. 6C) and 16 hrs post-infection (FIG. 6D) in PB as well as in heart (panel E), by using blood agar analysis of viable extracellular bacteria. Because neutrophil induction was not instigated by bacterial infection in GCSF or Am80 or Am80-GCSF mice, it indicates that significantly increased neutrophil bactericidal activity in Am80 mice results from Am80-promoted differentiation of existing granulocytic precursors into mature neutrophils at the earlier developmental stage of moue neutropenia. *: P<0.05; : P<0.01; *: P<0.005. A+G: Am80-GCSF.

Example 6: Use of Lower Dose with Addition of Am80-GCSF Group at Neutrophil-Decrease Stage Mice (C57BL6/J) were randomly divided into five groups (3 control and 4 for each experimental group, n=19 mice). C57BL/6J mice (n=19) were randomly divided into five groups (3 for control and 4 for each of experimental groups). The procedures for induction of mouse neutropenia and treatment are the same to the medium dose test (see slide 6). Mice were challenged with $6.3 \times 10^6$ CFU of S. aureus on day 2 via tail vein injection. After 3 hrs infection, each 100 µl blood was collected from tails for determining initial bactericidal activities of neutrophils. The mice were sacrificed on day 3, by which PB and spleen were harvested. (FIG. 7A). Vetscan analysis of WBC and neutrophils in PB was performed (FIG. 7B). Except blank mice, neutrophil induction was not observed in all other groups (FIG. 7C-E). Bactericidal activities of neutrophils were determined 3 hr (panel C) and 16 hrs post-infection (panel D) in PB as well as in spleen (panel E), using blood agar analysis of viable extracellular bacteria. Because neutrophil induction was not instigated by bacterial infection in GCSF or Am80 or Am80-GCSF mice, it indicates that significantly increased neutrophil bactericidal activity in Am80 mice results from Am80-promoted differentiation of existing granulocytic precursors into mature neutrophils at the earlier developmental stage of moue neutropenia. *: P<0.05; : P<0.01; *: P<0.005. Neutrophils induced by a lower dose of Am80 in neutropenic mice at the prevention stage display a greater bactericidal activity than those induced by G-CSF or Am80+GCSF.

Example 7: Use of Lower Dose with Addition of Am80-GCSF Group at Neutrophil-Recovery Stage Mice (C57BL6/J) were randomly divided into five groups (3 control and 4 for each experimental group, n=19 mice). As illustrated (FIG. 8a), mice were given regimens 2 days post-CPA injection (200 mg/kg). After consecutive 3 days of treatment, mice were challenged with S. Aureus for up to 16 hrs before euthanasia. We found a significant increase of peripheral blood (PB) neutrophils in all groups after bacterial infection (FIG. 8b). PB collected at 3 and 16 hrs-post infection was used for analyzing of neutrophil bactericidal activities. Independent killing assays showed that neutrophils induced by Am80-GCSF combination, but not by Am80 alone, killed significantly more bacteria (FIG. 8c). By assessing neutrophil production, we found that Am80 induced least number of neutrophils in both BM and PB than did GCSF or Am80-GCSF (FIG. 8d, 8e). Although GCSF induced significantly more neutrophils in BM while similar amount in PB compared to Am80-GCSF (FIG. 8d, 8e; lower panels), GCSF-induced neutrophils displayed significantly low bactericidal activity compared to those induced by Am80-GCSF (FIG. 8c). Moreover, neutrophils induced by Am80-GCSF combination displayed better granulocytic morphologic differentiation (FIG. 8d, 8e; left panels). These results indicate that during neutrophil-recovery when BM function is still inhibited, only fewer numbers of granulocytic precursors are available to be differentiated by Am80 into mature neutrophils, whereas large amount of neutrophils induced by GCSF are defective in bacterial killing. However, with low doses of Am80-GCSF treatment, Am80 can effectively differentiate GCSF-regenerated granulocytic precursors into mature neutrophils against microbial infection. P<0.05; : P<0.01; *: P<0.005.

Example 8: Use of Lower Dose of Am80-GCSF Combination Significantly Reduces Infection-Related Mortality of Neutropenic Mice Enduring Continual Bacteremia If Am80 can indeed differentiate GCSF-regenerated great amount of granulocytic precursors into mature neutrophils against infection, Am80-GCSF combination should effectively reduce infection-related mortality in cancer chemotherapy induced neutropenia. We tested this hypothesis by using neutropenic mice experiencing bacteremia through entire neutropenia period. As illustrated (FIG. 9A), mice were given different regimens 4 hrs post-CPA injection for up to day 8. S. Aureus infection was performed on day 3, and survival rate was calculated on day 9. With 3 independent experiments, we determined that Am80-GCSF increased the survival rate significantly more than did GCSF or Am80 alone (FIG. 9B-D). To evaluate bactericidal ability of regenerated neutrophils in survived mice, the survived blank and Am80-GCSF mice on day 11 were further infected with S. Aureus for 15 min before euthanasia. A parallel analysis of freshly isolated PB with both Giemsa and Gram stains determined neutrophil phagocytosis in infected mice vs. free of bacteremia in non-infected mice (FIG. 9E). Since GCSF is usually provided to CCIN ≥24 hrs post-chemo drug, we further tested low and medium doses of Am80-GCSF treatment 24 hrs post-CPA, as illustrated (FIG. 9F, 9J), with two independent experiments for each of doses. The results from low-dose test showed that GCSF group had only 12.5% survival rate, while no mortality was observed in either blank or Am80-GCSF group (FIG. 9g-i). However, in medium-dose test, the survival rate between Am80-GCF (55.6%) and GCSF (11.1%) groups had no statistical difference (FIG. 9K-M). Altogether, these survival mouse models demonstrate that low doses of Am80-GCSF reduce infection-related mortality of neutropenic mice.

Example 9: Effects of Am80 and RA in CD34+ Cells

Figure 10:
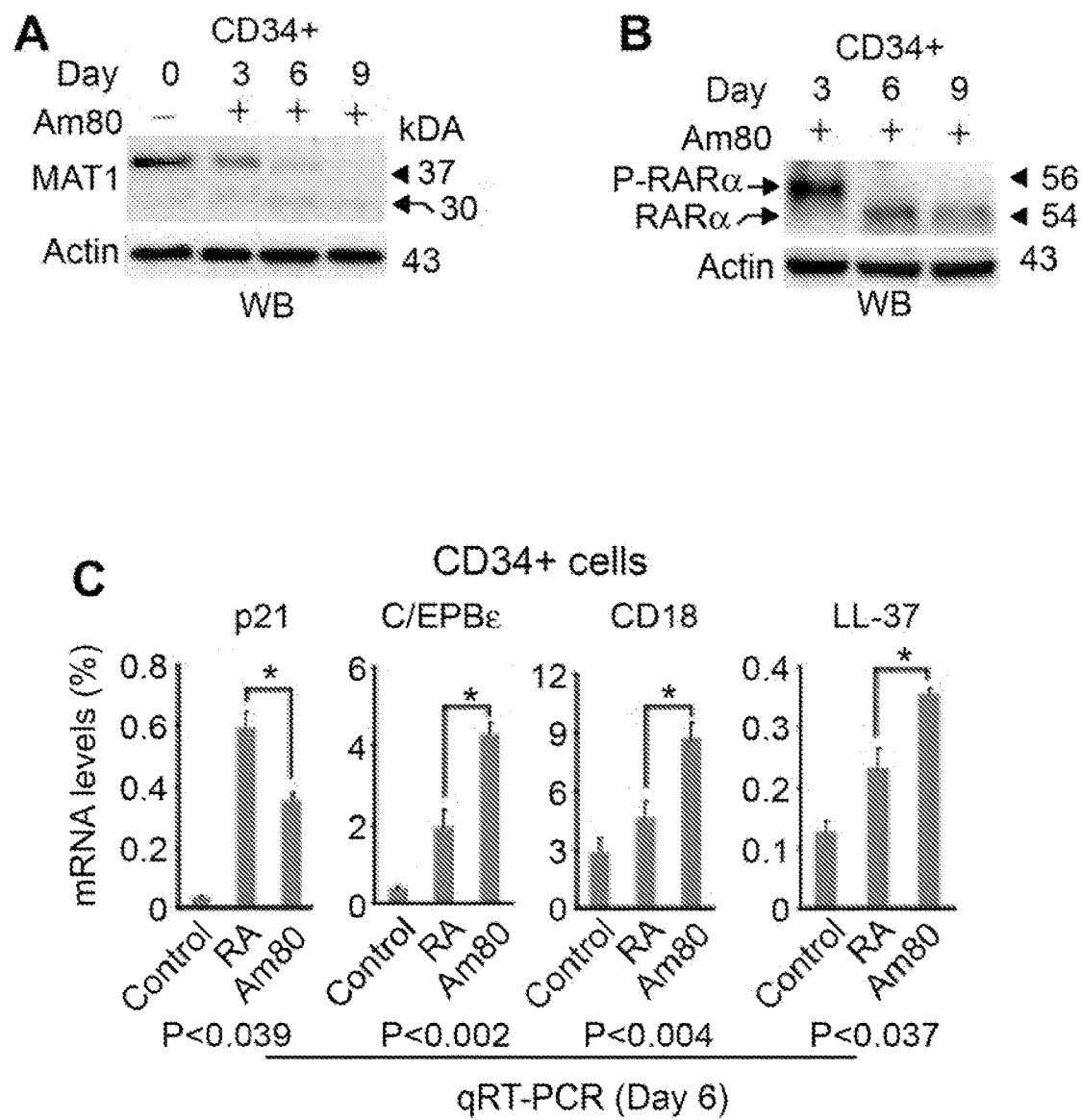
FIG. 10 depicts, in accordance with various embodiments of the invention, the molecular signaling of Am80.

Western blot depicting the progressive induction of MAT1 fragmentation (which is indicative of granulocytic differentiation) (FIG. 10A) and retinoic acid receptor (RARα) hypophosphorylation (i.e. decreased phosphorylation of RARα which is indicative of promotion of granulocytic differentiation) in CD34+ cells (FIG. 10B) by Am80. A novel gene transcription pattern is induced by Am80, in contrast to All-trans retinoic acid (ATRA or RA). A significant up-regulation of C/EBPε, CD18, and granule LL-37 and a decrease in p21Cip/Kip mRNA levels was observed following Am80 administration (FIG. 10C).

Example 10: Regimen Effects in Leukemic Cells and CD34+ Cells

Figure 11:
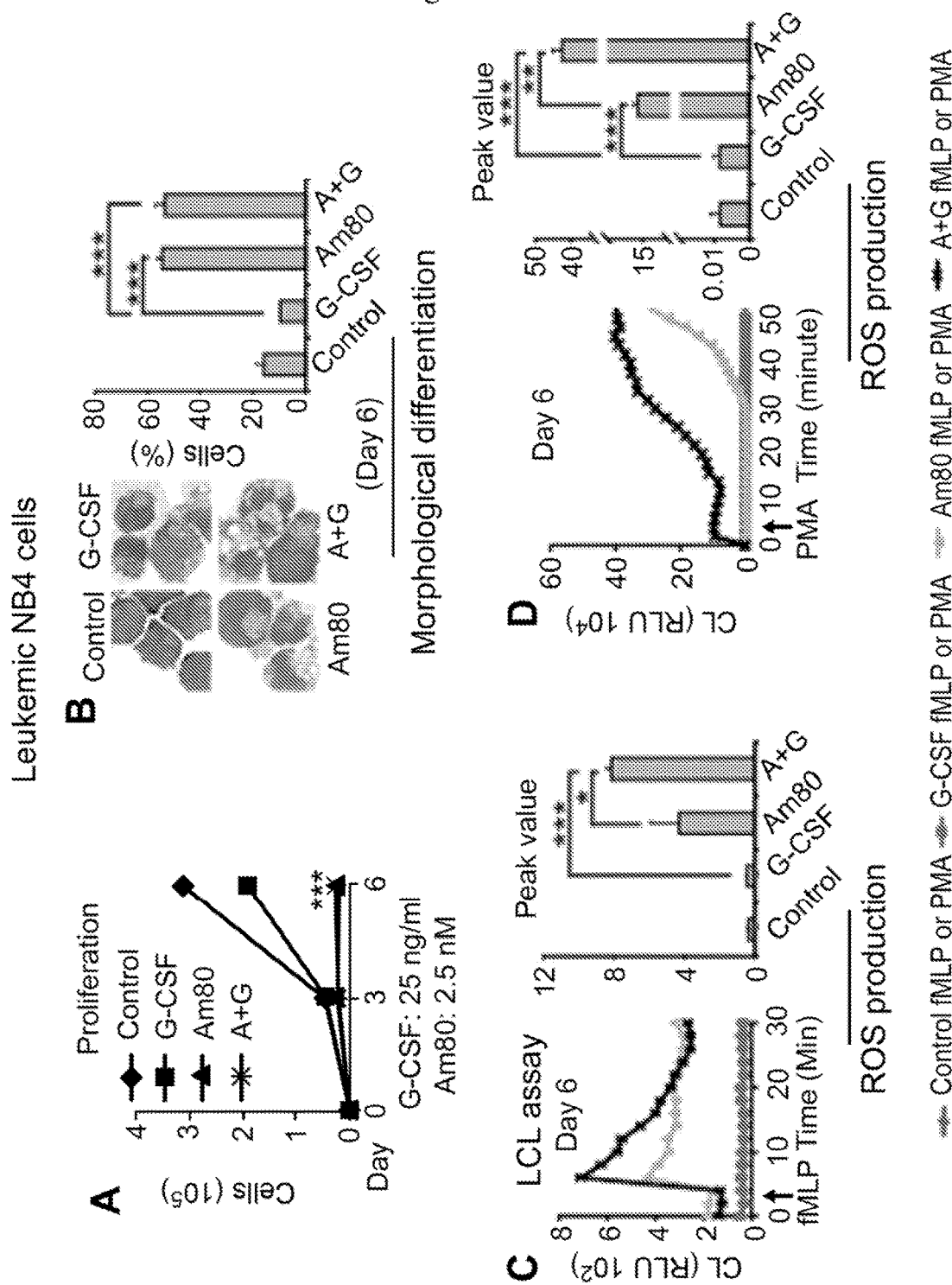
FIG. 11 depicts, in accordance with various embodiments of the invention, that the combination of Am80 and G-CSF promotes greater ROS production than Am80 or G-CSF alone while inhibiting leukemic growth.

Am80-GCSF inhibits NB4 cell proliferation (FIG. 11A) while significantly promoting granulocytic differentiation (FIG. 11B) and ROS production at day 6 in the presence of either Formyl-Methionyl-Leucyl-Phenylalanine (f-Met-Leu-Phe; fMLP) (FIG. 11C) or in the presence of PMA (FIG.

11D). *, P<0.04 at least. G-CSF fails to induce ROS production in NB4 cells in the presence of either fMLP or PMA.

Figure 12:
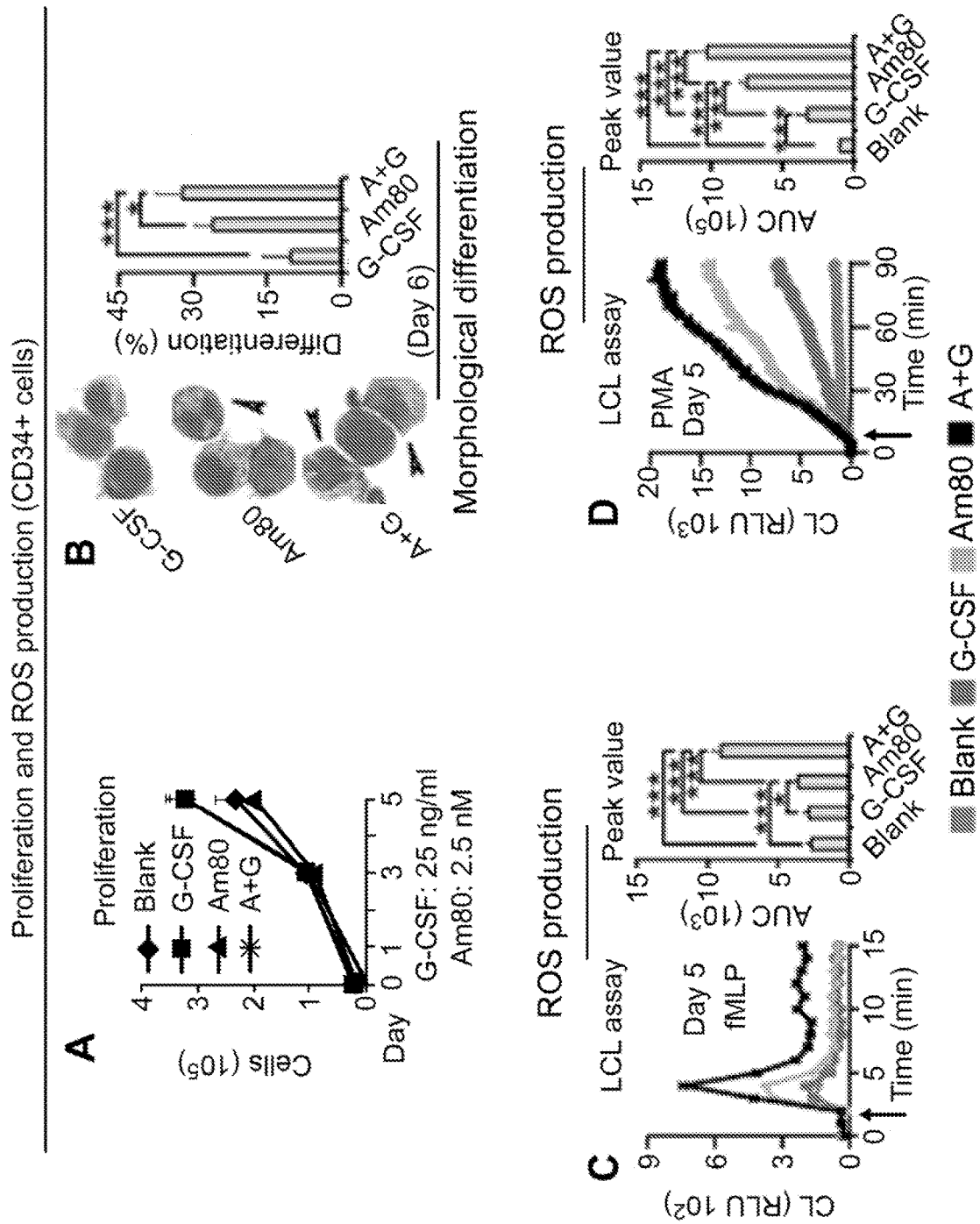
FIG. 12 depicts, in accordance with various embodiments of the invention, that the combination of Am80 and GCSF promotes greater ROS production than Am80 or G-CSF alone in normal hematopoietic $CD34^+$ precursor cells.

Am80-GCSF induces myelopoietic expansion similar to GCSF while promoting significantly greater neutrophil differentiation than Am80 or GCSF (FIG. 12A, 12B) and significantly higher ROS production at day 5 in the presence of either fMLP (FIG. 12C) or in the presence of PMA (FIG. 12D) compared to Am80 or GCSF alone. *, P<0.02 at least.

Example 11: AML Patient Blasts Following Am80 or GCSF or ATRA Treatment

Figure 13:
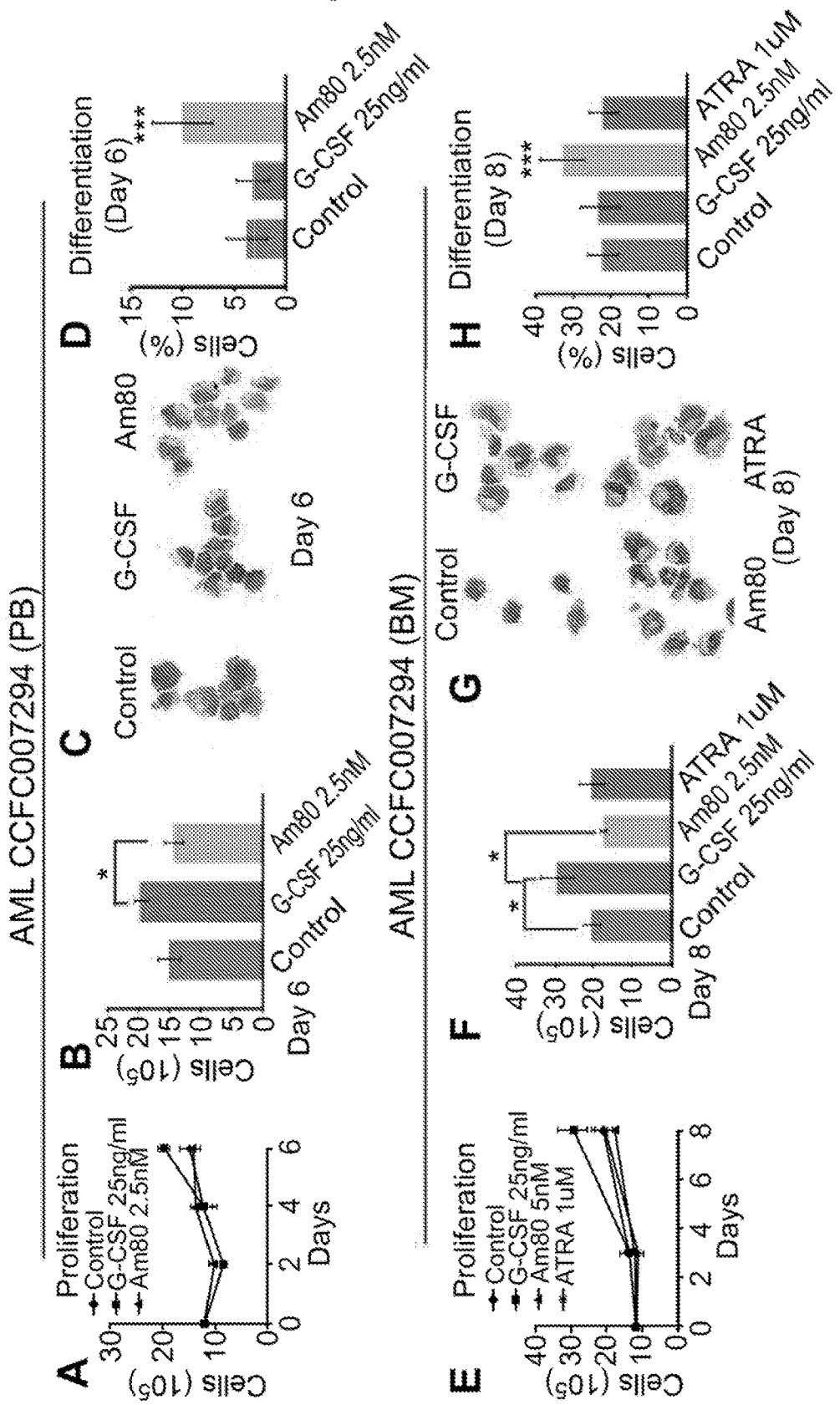
FIG. 13 depicts, in accordance with various embodiments of the invention, G-CSF treatment promotes the growth of non-APL (acute promyelocytic leukemia) AML patient blasts compared to those treated with Am80 or ATRA.
Figure 13:
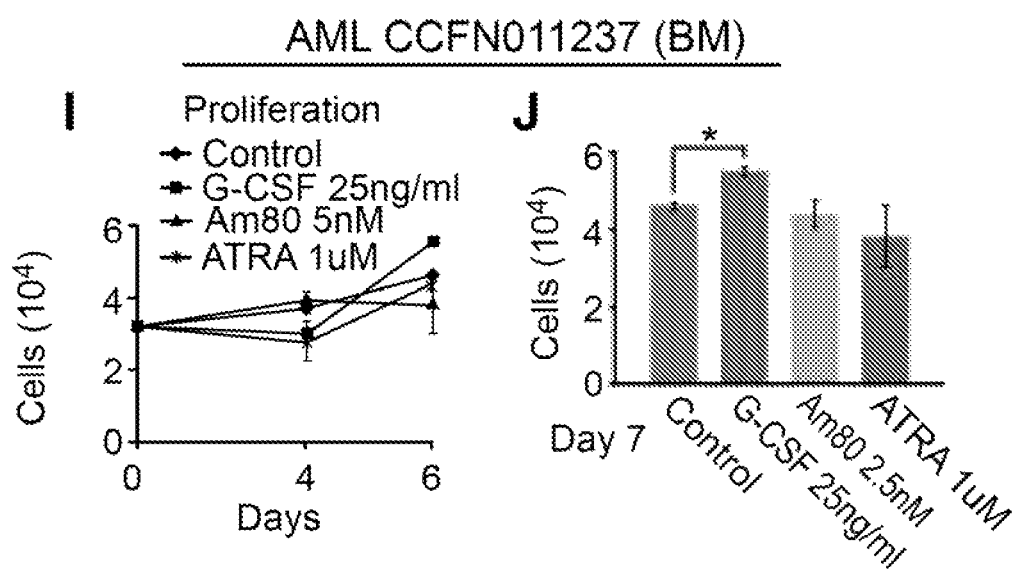

Proliferation of PB primary blasts from acute myeloid leukemia patients was assayed (FIG. 13A) and quantified P<0.05 (FIG. 13B). Granulocytic morphology of AML PB primary blasts was analyzed (FIG. 13C) and quantified; Am80 vs. G-CSF, P<4.0E-8; Am80 vs. control, P<6.02E-7 (FIG. 13D).

Proliferation of BM primary blasts from acute myeloid leukemia patients was assayed (FIG. 13E) and quantified at day 8, Am80 vs. G-CSF, P<0.008; G-CSF vs. control, P<0.032 (FIG. 13F). Granulocytic morphology of AML BM primary blasts was analyzed (FIG. 13G) and quantified; Am80 vs. G-CSF, P<9.9E-4; Am80 vs. RA, P<1.0E-4 (FIG. 13H). Higher growth rate was induced by G-CSF in AML BM primary blasts (FIG. 13I) and cell proliferation was quantified; G-CSF vs. control, P<0.018 (FIG. 13J). These data suggest that G-CSF treatment promotes the growth of non-APL (acute promyelocytic leukemia) AML patient blasts compared to those treated with Am80 or ATRA.

Figure 14:
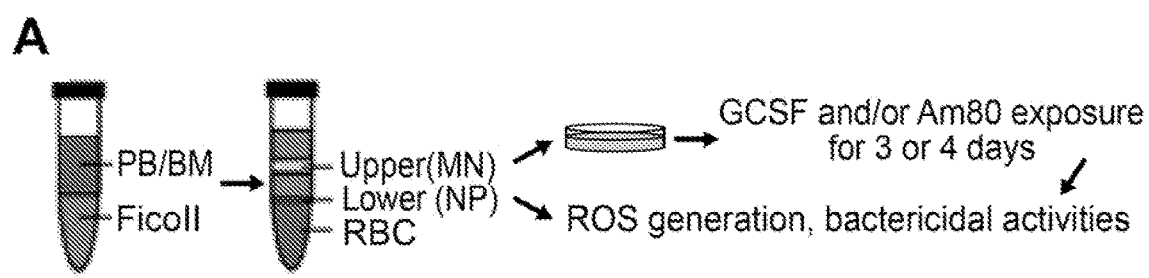
FIG. 14 depicts, in accordance with various embodiments of the invention, that Am80-GCSF significantly promotes ROS production in peripheral blood mononuclear cells isolated from healthy human donors.
Figure 14:
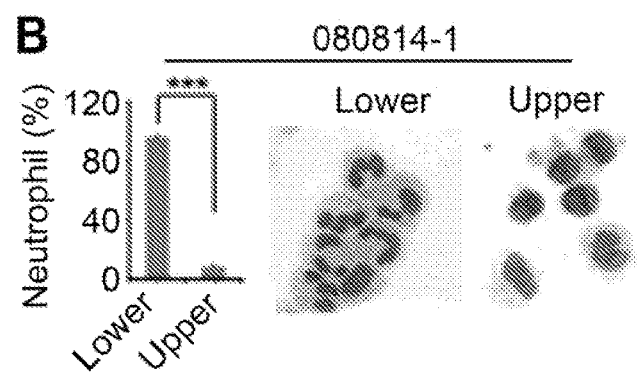
Figure 14:
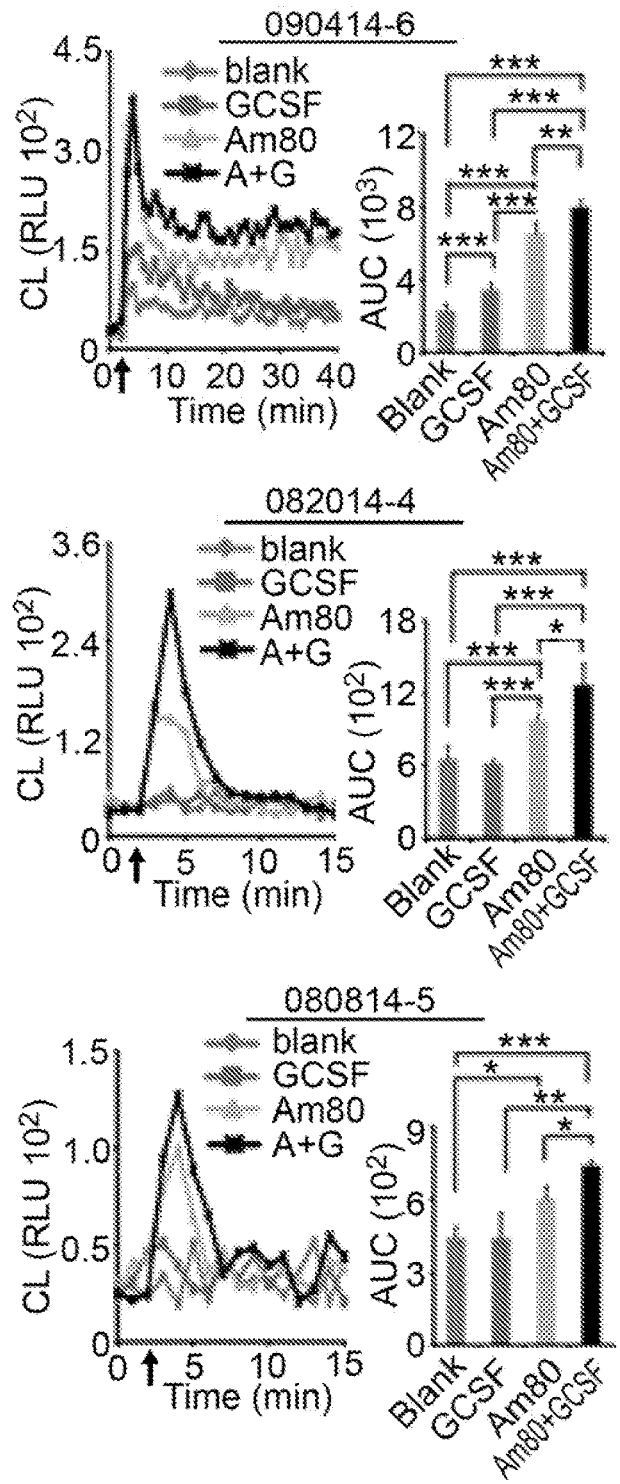
Figure 14:
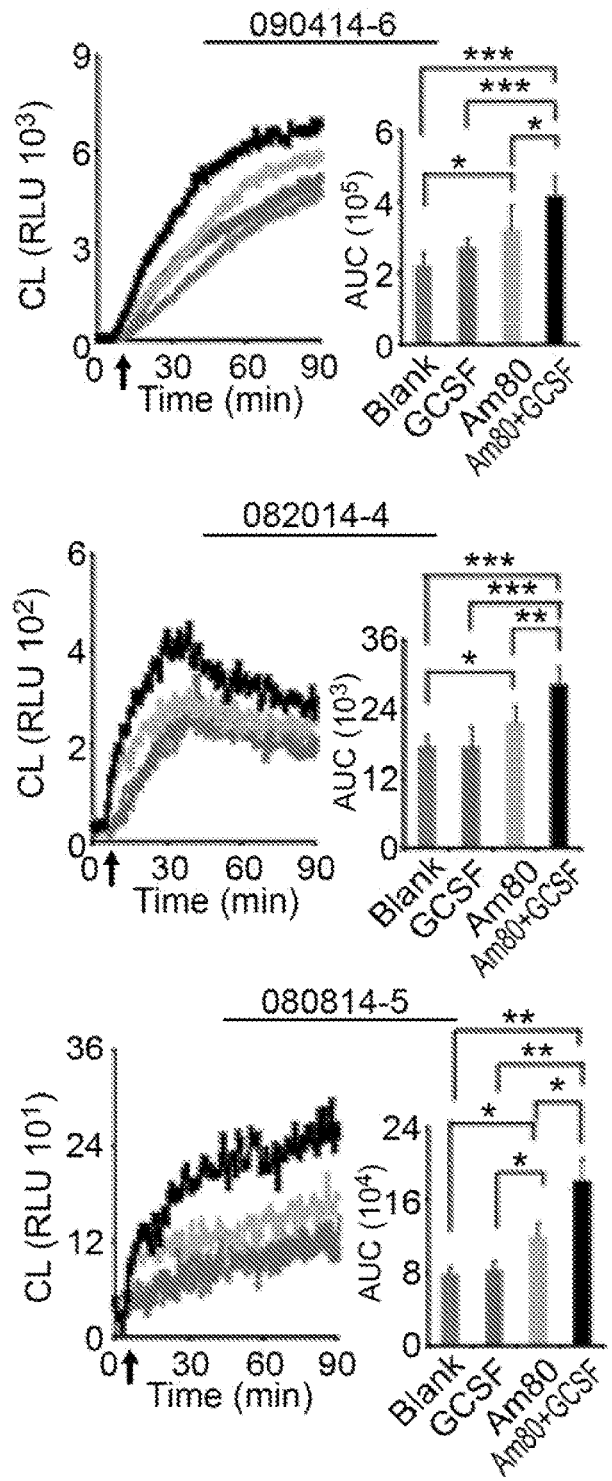

Example 12: Am80-GCSF Promotes ROS Production in Peripheral Blood Mononuclear Cells and in Bone Marrow (BM) Cells Upper layers of mononuclear cells were isolated from PB of three normal human donors and were cultured in granulocyte-lineage medium with low doses of Am80, GCSF, or Am80-GCSF for up to 4 days (FIG. 14A, B). In each of the donors, neutrophils induced by Am80-GCSF displayed significantly higher levels of ROS production in the presence of either fMLP (FIG. 14C) or PMA (FIG. 14D) compared to Am80 or GCSF alone. Am80-GCSF significantly promotes ROS production in peripheral blood mononuclear cells isolated from normal human donors.

Figure 15:
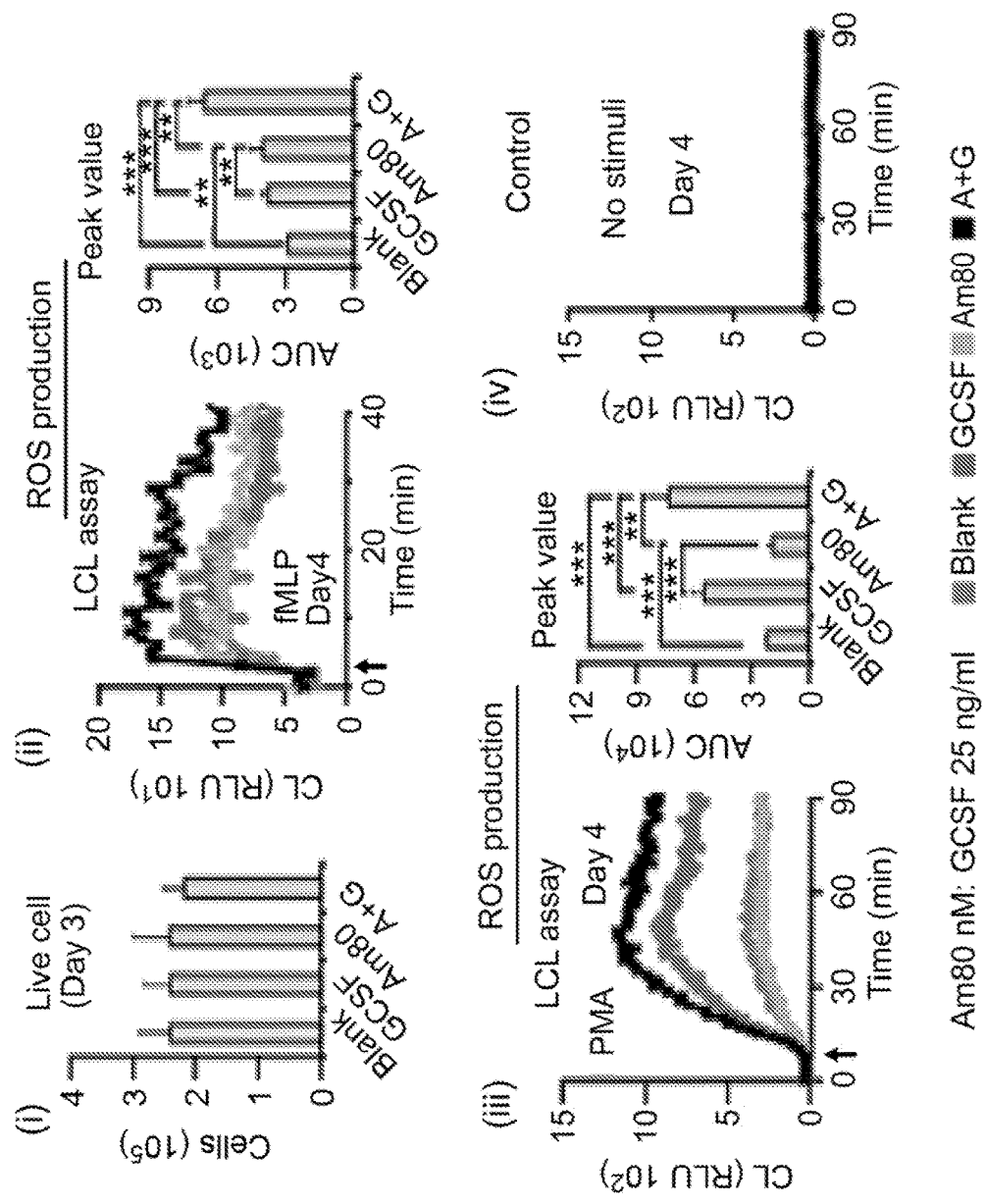
FIG. 15 depicts, in accordance with various embodiments of the invention, that Am80-GCSF promotes significantly greater ROS production in healthy bone marrow (BM) cells or peripheral blood (PB) mononuclear cells obtained from acute myeloid leukemia patients.
Figure 15:
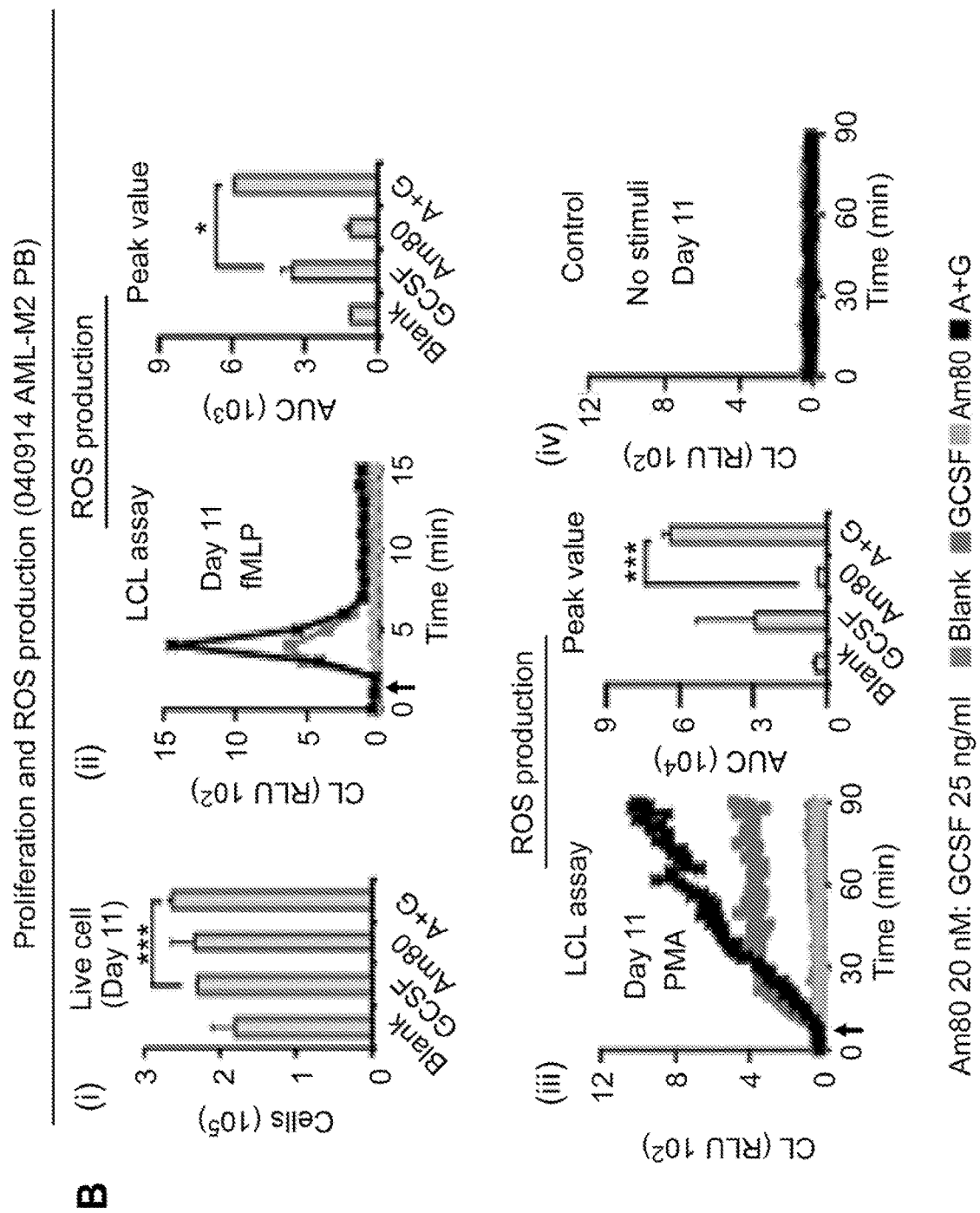
Figure 15:
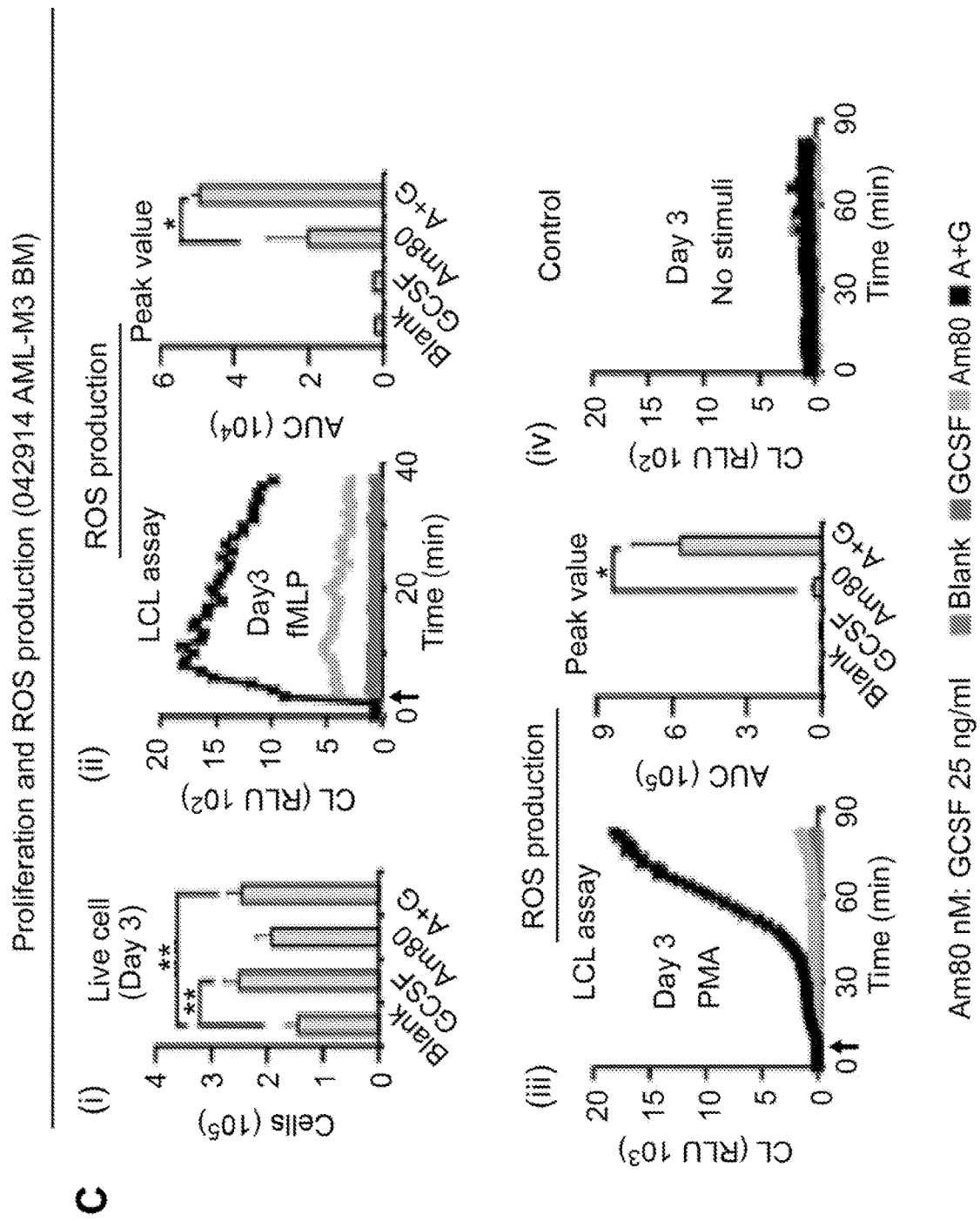

Bone marrow (BM) cells or peripheral blood (PB) mononuclear cells freshly isolated from acute myeloid leukemia (AML) patients were cultured in granulocyte-lineage induction medium and counted at day 3 (FIGS. 15A(i), 15B(i) and 15C(i)). ROS production was assayed in the presence of either fMLP (FIGS. 15A(ii), 15B(ii) and 15C(ii)) or PMA (FIGS. 15A(iii), 15B(iii) and 15C(iii)). Am80-GCSF promotes significantly greater ROS production compared to Am80 or GCSF alone The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of treating, reducing the likelihood of developing, reducing the severity of, and/or slowing the progression of neutropenia in a subject, comprising:
    administering a therapeutically effective amount of tamibarotene equivalent to 0.001 to 0.1 mg orally/kg per day, and administering a therapeutically effective amount of granulocyte colony-stimulating factor (G-CSF) or an analog thereof equivalent to 20 to 200 mcg subcutaneously/kg per period, to the subject,
    thereby treating, reducing the likelihood of having, reducing the severity of and/or slowing the progression of neutropenia in the subject,
    wherein the neutropenia comprises chemotherapy-induced neutropenia, congenital neutropenia, idiopathic neutropenia, cyclic neutropenia, or autoimmune neutropenia.

2. The method of claim 1, wherein the tamibarotene and the G-CSF or the analog thereof are provided in one composition or in separate compositions.

3. The method of claim 1, wherein the subject is a human.

4. The method of claim 1, wherein the tamibarotene and the G-CSF or the analog thereof are administered intravenously, intramuscularly, subcutaneously, intraperitoneally, orally or via inhalation.

5. The method of claim 1, wherein the tamibarotene and the G-CSF or the analog thereof are administered concurrently or sequentially.

6. The method of claim 1, wherein the tamibarotene is administered before, during or after administering the G-CSF or the analog thereof.

7. The method of claim 1, wherein the tamibarotene is administered at about 0.01 to 0.1 mg orally/kg per day.

8. The method of claim 1, wherein the tamibarotene is administered for about 20-30 days.

9. The method of claim 1, wherein the G-CSF or the analog thereof is administered per period of about 20-30 days.

10. A method of treating, reducing the likelihood of developing, reducing the severity of and/or slowing the progression of neutropenia in a subject, comprising:
    stimulating a cell with tamibarotene at a therapeutically effective amount equivalent to 0.001 to 0.1 mg orally/kg of the subject per day and with G-CSF or an analog thereof at a therapeutically effective amount equivalent to 20 to 200 mcg subcutaneously/kg of the subject per period, thereby generating granulocytes; and
    administering the generated granulocytes to the subject, thereby treating, reducing the likelihood of developing, reducing the severity of and/or slowing the progression of the neutropenia in the subject,
    wherein the neutropenia comprises chemotherapy-induced neutropenia, congenital neutropenia, idiopathic neutropenia, cyclic neutropenia, or autoimmune neutropenia.

11. The method of claim 10, wherein the granulocytes are neutrophils.

12. The method of claim 1, wherein the subject is a domestic or game animal selected from the group consisting of a cow, a horse, a pig, deer, a bison, a buffalo, a feline species, and a canine species.

13. The method of claim 1, wherein the tamibarotene is administered for about 1-10 days.

14. The method of claim 1, wherein the tamibarotene is administered for about 10-20 days.

15. The method of claim 1, wherein the G-CSF or the analog thereof is administered per period of about 1-10 days.

16. The method of claim 1, wherein the G-CSF or the analog thereof is administered per period of about 10-20 days.

17. The method of claim 1, the therapeutically effective amount of tamibarotene and the therapeutically effective amount of G-CSF or an analog thereof are administered at neutrophil-decrease stage.

* * * * *